United States Patent
Baranski et al.

(10) Patent No.: US 11,301,048 B2
(45) Date of Patent: Apr. 12, 2022

(54) WEARABLE DEVICE FOR DETECTING LIGHT REFLECTED FROM A USER

(71) Applicant: Apple Inc., Cupertino, CA (US)

(72) Inventors: Andrzej Baranski, Santa Clara, CA (US); Anna-Katrina Shedletsky, Mountain View, CA (US); Kuldeep P. Lonkar, Sunnyvale, CA (US); Serhan Isikman, Sunnyvale, CA (US); Stephen Brian Lynch, Portola Valley, CA (US); Colin M. Ely, Sunnyvale, CA (US); Christopher Werner, San Jose, CA (US); Erik De Jong, San Francisco, CA (US); Samuel B. Weiss, Los Altos Hills, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/869,877

(22) Filed: May 8, 2020

(65) Prior Publication Data

US 2020/0272240 A1    Aug. 27, 2020

Related U.S. Application Data

(63) Continuation of application No. 16/365,257, filed on Mar. 26, 2019, now Pat. No. 10,671,176, which is a
(Continued)

(51) Int. Cl.
*G06F 3/01* (2006.01)
*A61B 5/00* (2006.01)
(Continued)

(52) U.S. Cl.
CPC ............ *G06F 3/017* (2013.01); *A61B 5/0059* (2013.01); *A61B 5/11* (2013.01); *A61B 5/389* (2021.01);
(Continued)

(58) Field of Classification Search
CPC .......... G06F 3/017; G06F 1/163; G06F 3/014; G06F 3/015; G06F 2200/1637;
(Continued)

(56) References Cited

U.S. PATENT DOCUMENTS 5,483,261 A    1/1996 Yasutake
5,488,204 A    1/1996 Mead et al.
(Continued)

FOREIGN PATENT DOCUMENTS

EP    2290583    3/2011
EP    2698686    2/2014
(Continued)

OTHER PUBLICATIONS

Eisenstein, et al., "Analysis of Clustering Techniques to Detect Hand Signs," *Intelligent Multimedia, Video and Speech Processing*, 2001 International Symposium, Piscataway, New Jersey, IEEE, Apr. 1985, pp. 259-262.
(Continued)

*Primary Examiner* — David D Davis
(74) *Attorney, Agent, or Firm* — Brownstein Hyatt Farber Schreck, LLP

(57) ABSTRACT

This relates to a device that detects a user's motion and gesture input through the movement of one or more of the user's hand, arm, wrist, and fingers, for example, to provide commands to the device or to other devices. The device can include a plurality of myoelectric sensors configured to detect one or more electrical signals from a body part of a user indicative of one or more movements. A plurality of signals indicative of the detected one or more electrical signals may be generated. The device may also include a wireless communication transmitter configured to communicate with a peripheral device and a processor. The processor may be configured to receive the plurality of signals
(Continued)

from the plurality of myoelectric sensors, use the plurality of signals together to determine a gesture, and communicate one or more of: the plurality of signals and the gesture to the peripheral device.

21 Claims, 15 Drawing Sheets

Related U.S. Application Data continuation of application No. 14/616,573, filed on Feb. 6, 2015, now Pat. No. 10,488,936.

(60) Provisional application No. 62/057,890, filed on Sep. 30, 2014.

(51) Int. Cl.
 A61B 5/11 (2006.01)
 A61B 5/389 (2021.01)
 G06F 1/16 (2006.01)
 A61B 5/316 (2021.01)

(52) U.S. Cl.
 CPC .......... *A61B 5/6824* (2013.01); *A61B 5/7475* (2013.01); *G06F 1/163* (2013.01); *G06F 3/014* (2013.01); *G06F 3/015* (2013.01); *A61B 5/1125* (2013.01); *A61B 5/316* (2021.01); *A61B 5/4519* (2013.01); *A61B 5/4523* (2013.01); *A61B 2562/0219* (2013.01); *A61B 2562/0261* (2013.01); *G06F 2200/1637* (2013.01)

(58) Field of Classification Search
 CPC ..... A61B 5/389; A61B 5/7475; A61B 5/0059; A61B 5/11; A61B 5/6824; A61B 5/316; A61B 5/1125; A61B 5/4519; A61B 2562/0219; A61B 2562/0261; A61B 5/4523
 See application file for complete search history.

(56) References Cited

U.S. PATENT DOCUMENTS

| | | |
|---|---|---|
| 5,825,352 A | 10/1998 | Bisset et al. |
| 5,835,079 A | 11/1998 | Shieh |
| 5,880,411 A | 3/1999 | Gillespie et al. |
| 6,188,391 B1 | 2/2001 | Seely et al. |
| 6,244,873 B1 | 6/2001 | Hill et al. |
| 6,265,978 B1 | 7/2001 | Atlas |
| 6,310,610 B1 | 10/2001 | Beaton et al. |
| 6,323,846 B1 | 11/2001 | Westerman et al. |
| 6,547,728 B1 | 4/2003 | Cornuejols |
| 6,570,557 B1 | 5/2003 | Westerman et al. |
| 6,677,932 B1 | 1/2004 | Westerman |
| 6,690,387 B2 | 2/2004 | Zimmerman et al. |
| 6,747,632 B2 | 6/2004 | Howard |
| 6,888,536 B2 | 5/2005 | Westerman et al. |
| 7,015,894 B2 | 3/2006 | Morohoshi |
| 7,156,819 B2 | 1/2007 | Sieller et al. |
| 7,184,064 B2 | 2/2007 | Zimmerman et al. |
| 7,218,226 B2 | 5/2007 | Wehrenberg |
| 7,547,282 B2 | 6/2009 | Lo |
| 7,570,295 B2 | 8/2009 | Funato |
| 7,614,008 B2 | 11/2009 | Ording |
| 7,616,110 B2 | 11/2009 | Crump et al. |
| 7,633,076 B2 | 12/2009 | Huppi et al. |
| 7,653,883 B2 | 1/2010 | Hotelling et al. |
| 7,657,849 B2 | 2/2010 | Imran et al. |
| 7,663,607 B2 | 2/2010 | Hotelling et al. |
| 7,688,306 B2 | 3/2010 | Wehrenberg et al. |
| 7,844,914 B2 | 11/2010 | Andre et al. |
| 7,957,762 B2 | 6/2011 | Herz et al. |
| 8,006,002 B2 | 8/2011 | Kalayjian et al. |
| 8,170,656 B2 | 5/2012 | Tan et al. |
| 8,239,784 B2 | 8/2012 | Hotelling et al. |
| 8,279,180 B2 | 10/2012 | Hotelling et al. |
| 8,292,833 B2 | 10/2012 | Son et al. |
| 8,378,811 B2 | 2/2013 | Crump et al. |
| 8,381,135 B2 | 2/2013 | Hotelling et al. |
| 8,436,810 B2 | 5/2013 | Langereis |
| 8,447,704 B2 | 5/2013 | Tan et al. |
| 8,479,122 B2 | 7/2013 | Hotelling et al. |
| 8,606,022 B2 | 12/2013 | Yokono |
| 8,618,930 B2 | 12/2013 | Papadopoulos et al. |
| 8,631,355 B2 | 1/2014 | Murillo et al. |
| 8,634,808 B1 | 1/2014 | Zhong et al. |
| 8,669,842 B2 | 3/2014 | Lim et al. |
| 8,684,924 B2 | 4/2014 | Ouwerkerk et al. |
| 8,768,424 B2 | 7/2014 | Crowe et al. |
| 8,786,575 B2 | 7/2014 | Miller |
| 8,963,806 B1 | 2/2015 | Starner et al. |
| 9,037,530 B2 | 5/2015 | Tan et al. |
| 9,044,149 B2 | 6/2015 | Richards et al. |
| 9,081,542 B2 | 7/2015 | Dickinson et al. |
| 9,265,449 B2 | 2/2016 | Donaldson |
| 9,317,110 B2 | 4/2016 | Lutnick et al. |
| 9,348,458 B2 | 5/2016 | Hotelling et al. |
| 9,387,360 B2 | 7/2016 | Niederman |
| 9,389,694 B2 | 7/2016 | Ataee et al. |
| 9,442,570 B2 * | 9/2016 | Slonneger ............... G06F 3/017 |
| 9,483,123 B2 | 11/2016 | Aleem et al. |
| 9,526,421 B2 | 12/2016 | Papadopoulos et al. |
| 9,592,007 B2 | 3/2017 | Nuovo et al. |
| 9,668,676 B2 | 6/2017 | Culbert |
| 9,753,543 B2 | 9/2017 | Jeon et al. |
| 9,757,266 B2 | 9/2017 | Hoffman et al. |
| 9,770,185 B2 | 9/2017 | Wheeler et al. |
| 9,811,648 B2 | 11/2017 | Choi et al. |
| 9,848,825 B2 | 12/2017 | Morris |
| 9,880,632 B2 | 1/2018 | Ataee et al. |
| 9,910,508 B2 | 3/2018 | Presura |
| 9,933,937 B2 | 4/2018 | Lemay et al. |
| 9,939,899 B2 | 4/2018 | Allee et al. |
| 9,946,395 B2 | 4/2018 | Zhang et al. |
| 10,042,422 B2 | 8/2018 | Morun et al. |
| 10,088,924 B1 | 10/2018 | Ivanchenko |
| 10,152,082 B2 | 12/2018 | Bailey |
| 10,478,099 B2 | 11/2019 | Lor et al. |
| 10,488,936 B2 | 11/2019 | Baranski et al. |
| 10,503,254 B2 | 12/2019 | Allee et al. |
| 2002/0024500 A1* | 2/2002 | Howard ............... G06F 3/0421 345/158 |
| 2005/0234351 A1* | 10/2005 | Nishii ............... A61B 5/02 600/503 |
| 2006/0033724 A1 | 2/2006 | Chaudhri et al. |
| 2006/0197753 A1 | 9/2006 | Hotelling |
| 2009/0174578 A1* | 7/2009 | Taki ............... G01B 11/03 341/20 |
| 2010/0182126 A1 | 7/2010 | Martis et al. |
| 2011/0054360 A1* | 3/2011 | Son ............... A61B 5/1126 600/595 |
| 2011/0148568 A1* | 6/2011 | Lim ............... G05B 19/042 340/4.31 |
| 2012/0127070 A1* | 5/2012 | Ryoo ............... G06F 3/014 345/156 |
| 2014/0028546 A1* | 1/2014 | Jeon ............... G06F 3/04842 345/156 |
| 2014/0031698 A1* | 1/2014 | Moon ............... A61B 5/6825 600/476 |
| 2014/0094675 A1 | 4/2014 | Luna et al. |
| 2014/0240103 A1 | 8/2014 | Lake et al. |
| 2014/0282270 A1* | 9/2014 | Slonneger ............... G06F 3/017 715/863 |
| 2015/0019135 A1 | 1/2015 | Kacyvenski et al. |
| 2015/0193102 A1 | 7/2015 | Lanier et al. |
| 2015/0366504 A1 | 12/2015 | Connor |
| 2016/0085296 A1 | 3/2016 | Mo et al. |
| 2017/0031453 A1* | 2/2017 | Presura ............... G06F 3/011 |
| 2018/0307314 A1 | 10/2018 | Connor |

(56) References Cited

U.S. PATENT DOCUMENTS

| | | |
|---|---|---|
| 2019/0000354 A1 | 1/2019 | Lor et al. |
| 2019/0220099 A1 | 7/2019 | Baranski et al. |
| 2020/0117272 A1 | 4/2020 | Allee et al. |

FOREIGN PATENT DOCUMENTS

| | | |
|---|---|---|
| JP | 2000163031 | 6/2000 |
| JP | 2002342033 | 11/2002 |
| KR | 20120054809 | 5/2012 |
| WO | WO 12/138663 | 10/2012 |
| WO | WO 14/117125 | 7/2014 |
| WO | WO 15/060856 | 4/2015 |
| WO | WO 15/119637 | 8/2015 |
| WO | WO 15/121100 | 8/2015 |
| WO | WO 16/053459 | 4/2016 |
| WO | WO 17/052957 | 3/2017 |

OTHER PUBLICATIONS

Lee, et al., "A Multi-Touch Three Dimensional Touch-Sensitive Tablet," *Proceedings of CHI: ACM Conference on Human Factors in Computing Systems*, Apr. 1985, pp. 21-25.

Morganti, et al., "A smart watch with embedded sensors to recognize objects, grasps and forearm gestures," *SciVerse Science Direct, Engineering Procedia*, available online at www.sciencedirect.com, 2012, pp. 1169-1175.

Reuss, et al., "Period Domain Analysis in Fetal Pulse Oximetry," *Proceedings of the Second Joint EMBS/BMES Conference*, Houston, Texas, Oct. 23-26, 2001, 2 pages.

Rubine, "The Automatic Recognition of Gestures," CMU-CS-91-202, submitted in Partial Fulfillment of the Requirements for the Degree of Doctor of Philosophy in Computer Science at Carnegie Mellon University, Dec. 1991, 285 pages.

Rubine, "Combining Gestures and Direct Manipulation," CHI 1992, pp. 659-660.

Westerman, "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, Spring 1999, 364 pages.

Zhao, et al., "Wireless Photoplethysmograph Knuckle Sensor System for Measuring Finger Motions," *2014 International Symposium on Optomechatronic Technologies*, IEEE, Nov. 5, 2014, pp. 205-209.

Zheng, et al., "An Efficient User Verification System via Mouse Movements," *Computer and Communications Security, ACM*, 2 Penn Plaza, New York, New York, Oct. 17, 2011, pp. 139-150.

\* cited by examiner

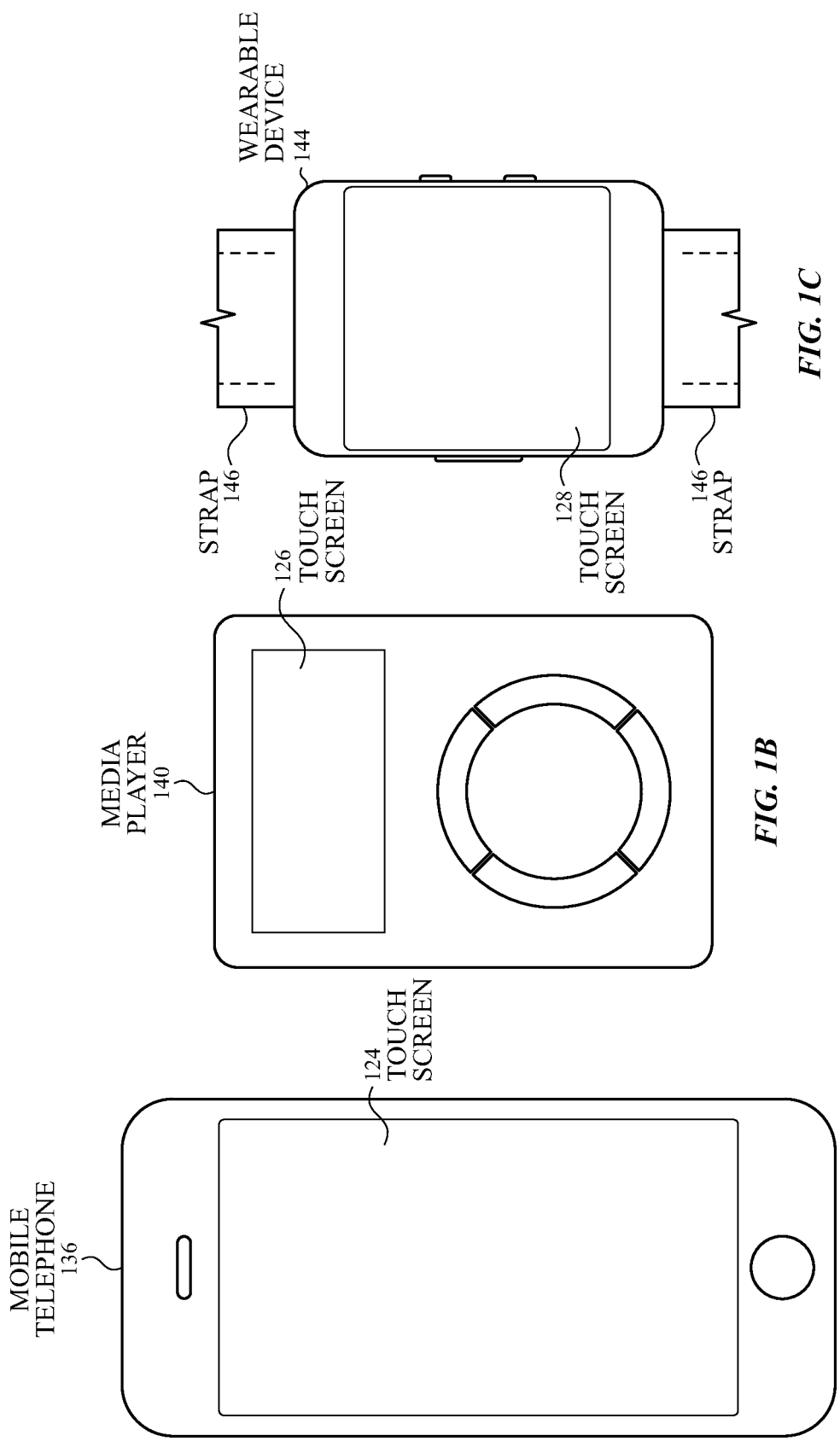

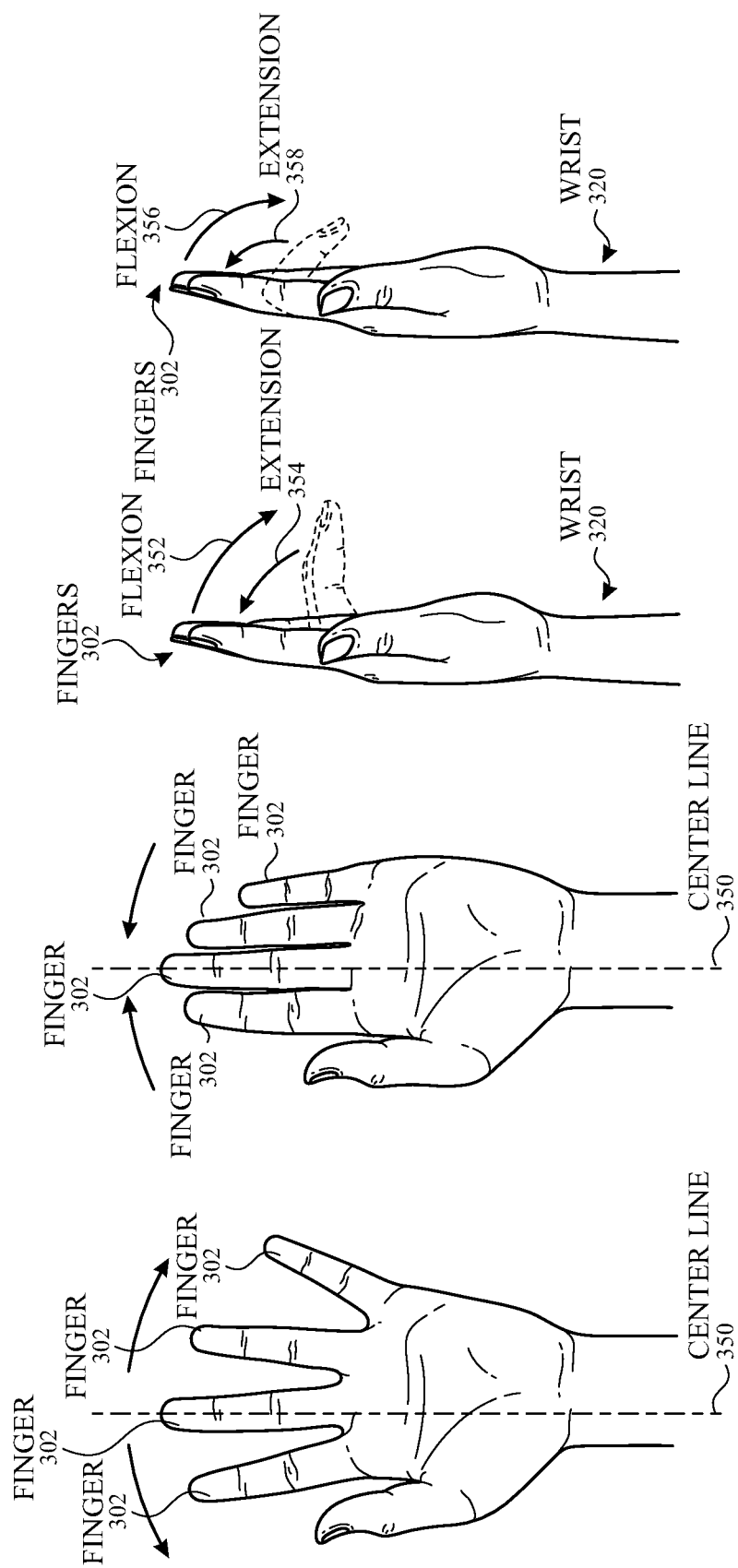

| GESTURE INPUTS | COMMAND |
| --- | --- |
| 1. HAND DOWN<br>2. PALM DOWN<br>3. PAUSE | DECLINE INCOMING PHONE CALL |
| HAND UP/DOWN AT A NORMAL SPEED | INCREASE OR DECREASE VOLUME ON SPEAKERS |
| HAND DOWN AT FAST SPEED | MUTE SPEAKERS |
| HAND WAVE ACROSS | SCROLL TO NEXT PAGE |
| HAND MOVEMENT TOWARDS USER | FIND PHONE OR ACTIVATE RINGER |
| THUMB AND LITTLE FINGERS EXTENDED WITH ALL OTHER FINGERS FIXED | MAKE A PHONE CALL |
| 1. FIXED FINGERS<br>2. EXTENDED FINGERS | UNLOCK CAR DOOR (WHILE USER APPROACHING OR CLOSE TO A CAR) |

*FIG. 9A*

WEARABLE DEVICE FOR DETECTING LIGHT REFLECTED FROM A USER

CROSS-REFERENCE TO RELATED APPLICATIONS

This application is a continuation of U.S. patent application Ser. No. 16/365,257, filed Mar. 26, 2019, which is a continuation of U.S. patent application Ser. No. 14/616,573, filed Feb. 6, 2015, now U.S. Pat. No. 10,488,936, which claims the benefit under 35 U.S.C. § 119(e) of U.S. Provisional Patent Application No. 62/057,890, filed Sep. 30, 2014, the contents of which are incorporated herein by reference as if fully disclosed herein.

FIELD

This relates generally to a device that detects a user's motion and gesture input to provide commands to the device or to other devices. In particular, the device can use one or more sensors to determine a user's motion and gesture input based on movements of the user's hand, arm, wrist, and fingers.

BACKGROUND

Many existing portable electronic devices use voice or touch input as a method for the user to communicate commands to the devices or to control the devices. One example is a voice command system, which can map specific verbal commands to operations, for example, to initiate dialing of a telephone number by speaking the person's name. Another example is a touch input system, where the user can choose a specific device setting, such as adjusting the volume of the speakers, by touching a series of virtual buttons or performing a touch gesture. While voice and touch input can be an effective way to control a device, there may be situations where the user's ability to speak the verbal command or perform the touch gesture may be limited.

SUMMARY

This relates to a device that detects a user's motion and gesture input through the movement of one or more of the user's hand, arm, wrist, and fingers, for example, to provide commands to the device or to other devices. The device can be attached to, resting on, or touching the user's wrist, ankle or other body part. One or more optical sensors, inertial sensors, mechanical contact sensors, and myoelectric sensors, to name just a few examples, can detect movements of the user's body. Based on the detected movements, a user gesture can be determined. The device can interpret the gesture as an input command, and the device can perform an operation based on the input command. By detecting movements of the user's body and associating the movements with input commands, the device can receive user input commands through another means in addition to, or instead of, voice and touch input, for example.

BRIEF DESCRIPTION OF THE DRAWINGS

FIGS. 1A-1C illustrate systems in which examples of the disclosure can be implemented.

FIGS. 3A-3H illustrate exemplary finger and wrist movements according to examples of the disclosure.

FIG. 9A illustrates exemplary gestures and corresponding commands according to examples of the disclosure.

DETAILED DESCRIPTION

Figure 2A:
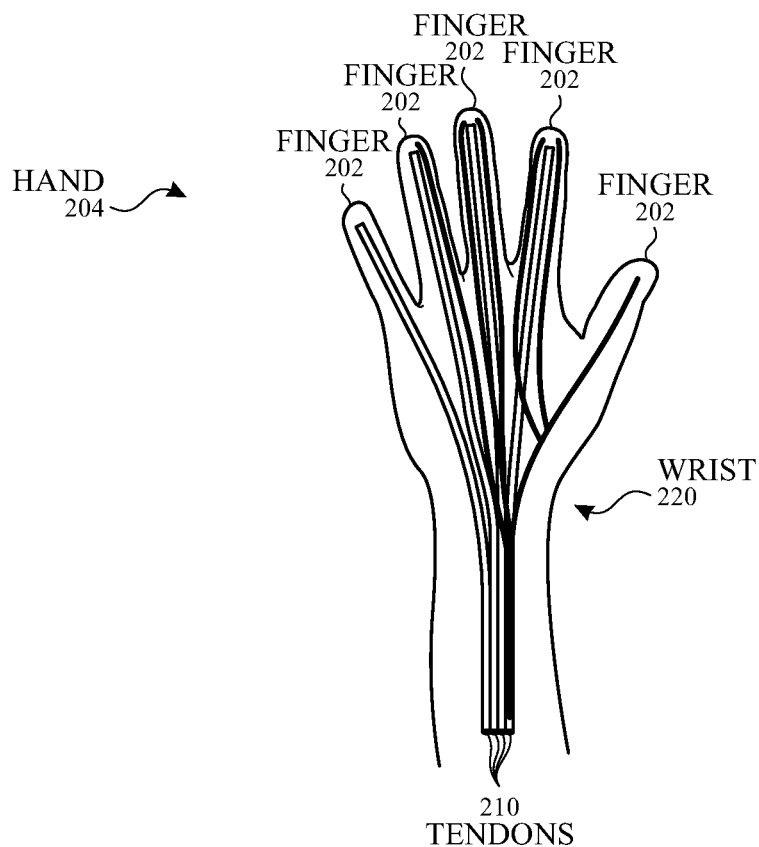
FIG. 2A illustrates an exemplary depiction of a human hand according to examples of the disclosure.

In the following description of examples, reference is made to the accompanying drawings in which it is shown by way of illustration specific examples that can be practiced. It is to be understood that other examples can be used and structural changes can be made without departing from the scope of the various examples.

Various techniques and process flow steps will be described in detail with reference to examples as illustrated in the accompanying drawings. In the following description, numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

Further, although process steps or method steps can be described in a sequential order, such processes and methods can be configured to work in any suitable order. In other words, any sequence or order of steps that can be described in the disclosure does not, in and of itself, indicate a requirement that the steps be performed in that order. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modification thereto, does not imply that the illustrated process or any of its steps are necessary to one or more of the examples, and does not imply that the illustrated process is preferred.

This disclosure relates to a device that detects a user's motion and gesture input to provide commands to the device or to other devices. The device can be attached to, resting on, or touching a user's wrist, ankle or other body part. One or more optical sensors, inertial sensors, mechanical contact sensors, and myoelectric sensors, to name just a few examples, can allow the device to detect movements of a user's body, such as the user's hand, arm, wrist, and fingers. Based on the detected movements, a user gesture can be determined. The device can interpret the gesture as an input command, and the device can perform an operation based on the input command. By detecting movements of the user's body and associating the movements with input commands, the device can receive user input commands through another means in addition to, or instead of, voice and touch input, for example.

In some examples, optical sensing can employ light sources and light sensors located on the device itself or located in the strap attached to the device. The light sources and light sensors can generate a reflectance profile from the reflectance of the light off the user's tendons, skin, muscles, and bones. In some examples, inertial sensing can employ an accelerometer and gyroscope to determine rigid body motions based on the change in motion along the axes and the change in orientation of the device attached to, resting on, or touching the user's hand, ankle or other body part. In some examples, mechanical contact sensing can be employed by using at least one flexible material around the user's body part, such as the wrist, that conforms to the user's movement. In some examples, myoelectric sensors can allow the device to detect the electrical signal or the change in capacitance in the tendons coupled with the user's movement.

Representative applications of methods and apparatus according to the present disclosure are described in this section. These examples are being provided solely to add context and aid in the understanding of the described examples. It will thus be apparent to one skilled in the art that the described examples may be practiced without some or all of the specific details. Other applications are possible, such that the following examples should not be taken as limiting.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can attach to a user using a strap 146. The systems of FIGS. 1A-1C be configured for optical sensing, inertial sensing, mechanical contacting sensing, myoelectric sensing, or a combination of two or more to determine a user's motion and gesture, as will be disclosed.

Figure 2B:
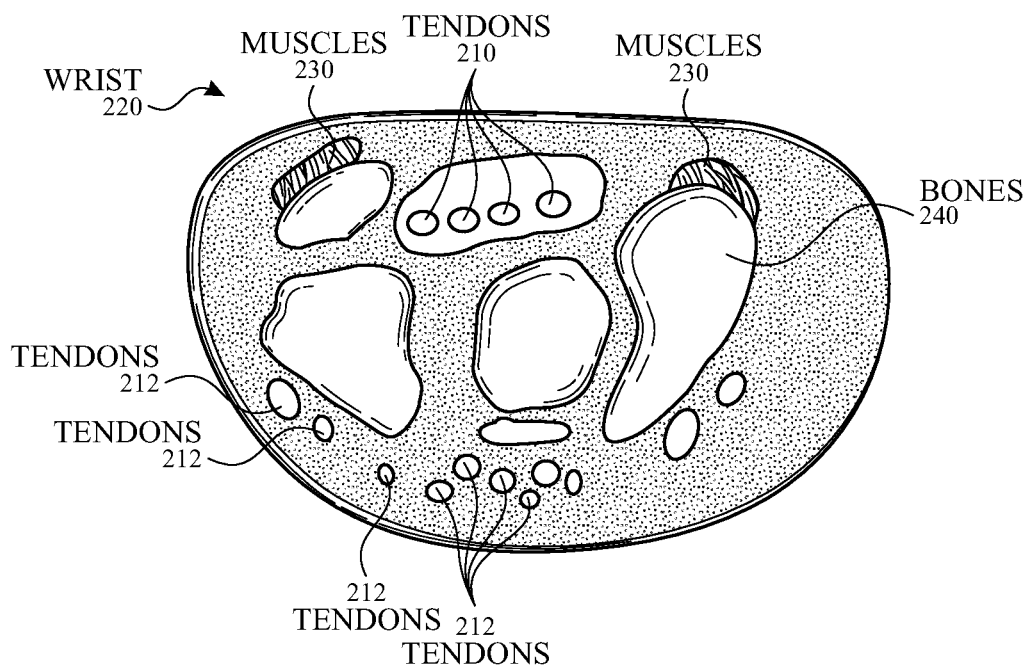
FIG. 2B illustrates a cross-sectional view of a human wrist according to examples of the disclosure.

FIG. 2A illustrates an exemplary depiction of a human hand, and FIG. 2B illustrates a cross-sectional view of a human wrist. It should be noted that although examples of the disclosure may be provided primarily with respect to a device attached to a user's wrist, and may primarily illustrate motions of the user's fingers, hand, or arm, other body parts such as ankles, knees, or the head (to name just a few examples) and their associated movements are also contemplated and fall within the scope of this disclosure. Hand 204 can include a plurality of fingers 202, a wrist 220, a plurality of tendons 210 and 212, a plurality of muscles 230, and a plurality of bones 240. Tendons 210 can be located on the palm-side of the hand, also known as the palmar side. Tendons 210 can also be referred to as flexor tendons. Tendons 212 can be located on a front side of the hand, also known as the dorsal side. Tendons 212 can also be referred to as extensor tendons. The hand muscles 230 are attached to bones 240 through the plurality of tendons 210 and 212. When a human moves a muscle or a bone, the human brain sends an electrical signal through the nervous system to the corresponding nerve. The nerve stimulates the muscle with the electrical signal, causing the muscle to contract or move. Muscle movement can lead to bone movement through the attached one or more tendons.

Figure 3H:
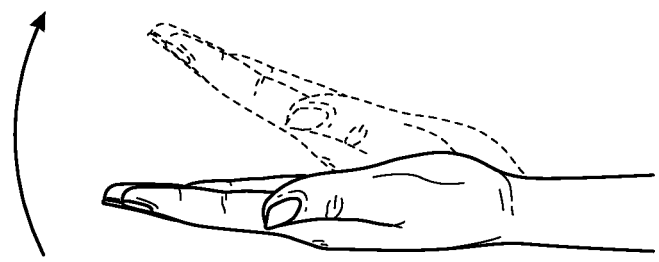

FIGS. 3A-3H illustrate exemplary finger and wrist movements. FIG. 3A illustrates abduction of the fingers 302 that can involve abductor muscles. As used herein, the term "abductors" generally refers to muscles that cause movement away from the center line 350. FIG. 3B illustrates adduction of the fingers 302 that can involve adductor muscles. As used herein, the term "adductors" generally refers to muscles that cause movement towards the center line 350.

Each finger (except the thumb) can include three joints: the metacarpophalangeal (MCP) joint, proximal interphalangeal (PIP) joint, and distal interphalangeal (DIP) joint. The MCP joints, also known as the knuckles, are located between the hand and fingers. The PIP joints are the next set of joints toward the fingernail, and the DIP joints are the farthest joints of the finger. Abduction of the fingers 302, as illustrated in FIG. 3A, and adduction of the fingers 302, as illustrated in FIG. 3B, can involve moving the MCP joint.

FIGS. 3C-3D illustrate flexion and extension of one or more fingers 302. Flexions 352 and 356 can involve muscles and tendons that bend one or more fingers 302 towards wrist 320. Flexion 352 can involve the MCP joint, whereas flexion 356 can involve PIP and DIP joints. Extensions 354 and 358 can involve muscles and tendons that cause movement of one or more fingers 302 away from wrist 320 and can involve all three MCP, PIP, and DIP joints. In some examples, finger flexion can include flexion of the thumbs, which can result in the user making a fist, for example.

Figure 3G:
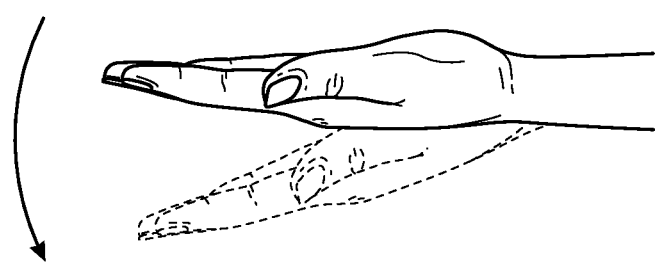
Figure 3F:
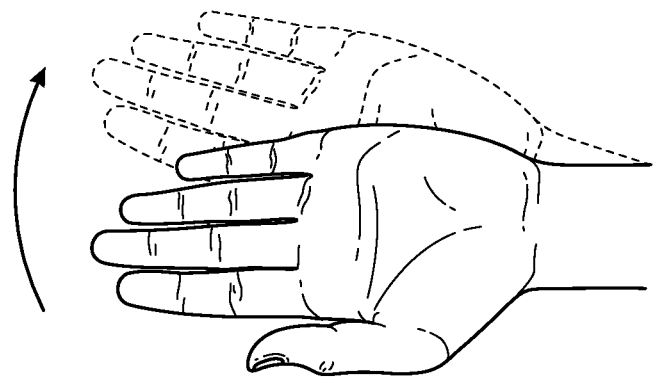
Figure 3E:
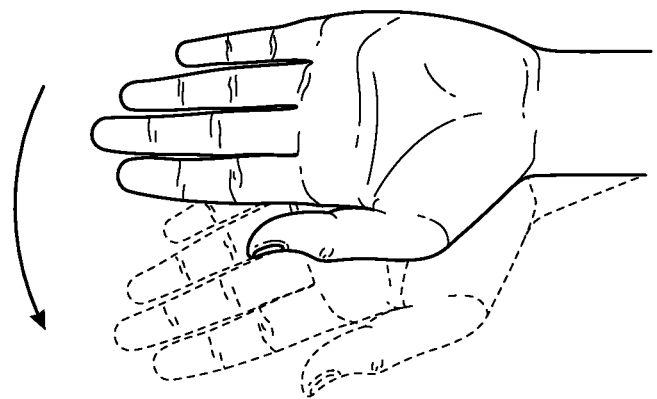

FIG. 3E illustrates wrist abduction, and FIG. 3F illustrates wrist adduction where the user can cause the wrist to move to one of the sides. Wrist abduction or radial deviation, as shown in FIG. 3E, can involve movement of the thumb side of the hand towards the radial side of the forearm. Wrist adduction or ulnar deviation, as shown in FIG. 3F, can involve movement of the little finger side of the hand towards the ulnar side of the forearm. FIG. 3G illustrates wrist extension, and FIG. 3H illustrates wrist flexion. Wrist extension can involve movement of the palm of the hand toward the dorsal side of the forearm. Wrist flexion can involve movement of the palm of the hand toward the inside of the forearm.

Figure 4:
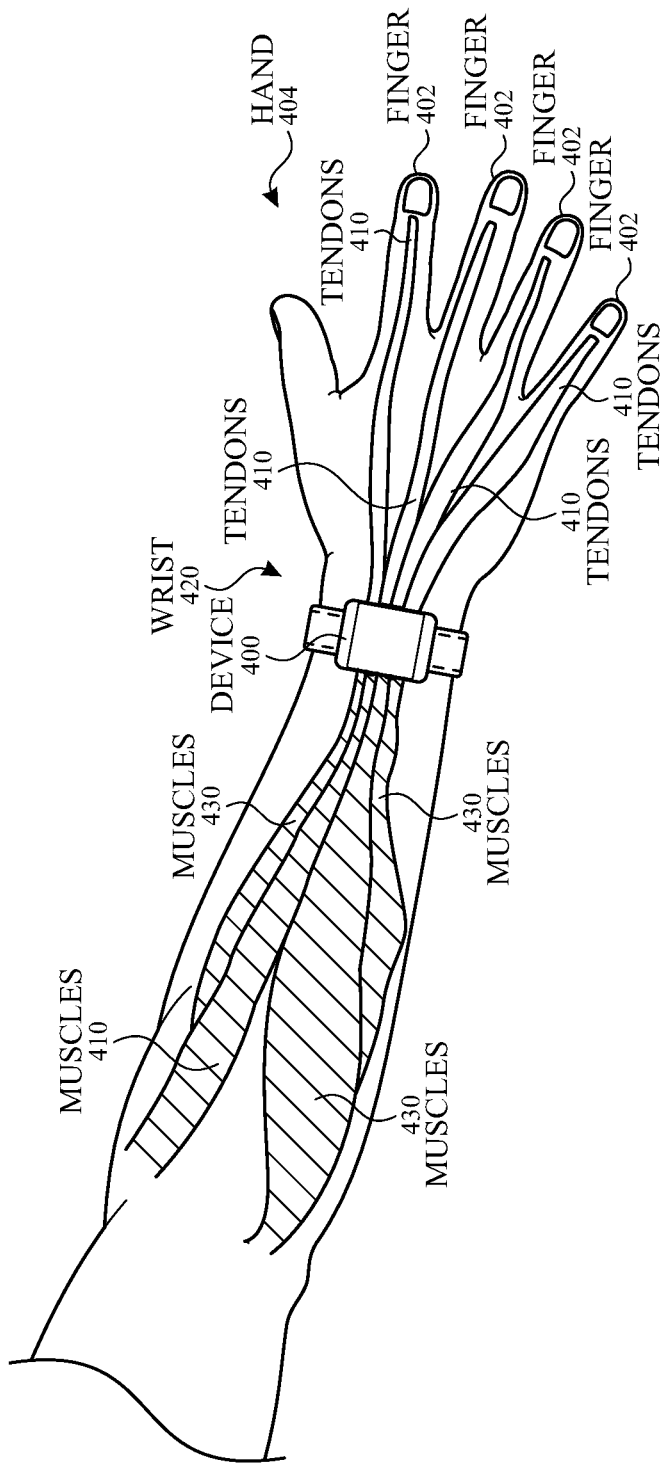
FIG. 4 illustrates an exemplary configuration of a wearable device attached to the wrist of a user according to examples of the disclosure.

FIG. 4 illustrates an exemplary configuration of a wearable device attached to a wrist according to examples of the disclosure. A user's arm can include fingers 402, hand 404, and wrist 420. Device 400 can be attached to, resting on, or touching a user's skin at any body part, such as the user's wrist 420. Muscles 430 can be attached to the bones in fingers 402 through tendons 410. When a user wants to perform any one of the movements illustrated in FIGS. 3A-3H, fingers 402, wrist 420, and hand 404 can move when the user's brain sends electrical signals to stimulate muscles 430. Muscles 430 can contract in response to the received electrical signals. In response to the received electrical signals, tendons 410, attached to muscles 430, can also contract or move and can cause move fingers 402, wrist 420, and hand 404 to move. As the tendons contract or move, device 400 can detect the movement of the tendons, the electrical signal, or both. Based on either the tendon movement or electrical signal or both, device 400 can determine the user's motion and gesture. The motion and gesture can be interpreted as commands to the device or another device. In some examples, a host device can perform the determination of the user's motion and gesture, as will be described below.

Figure 5A:
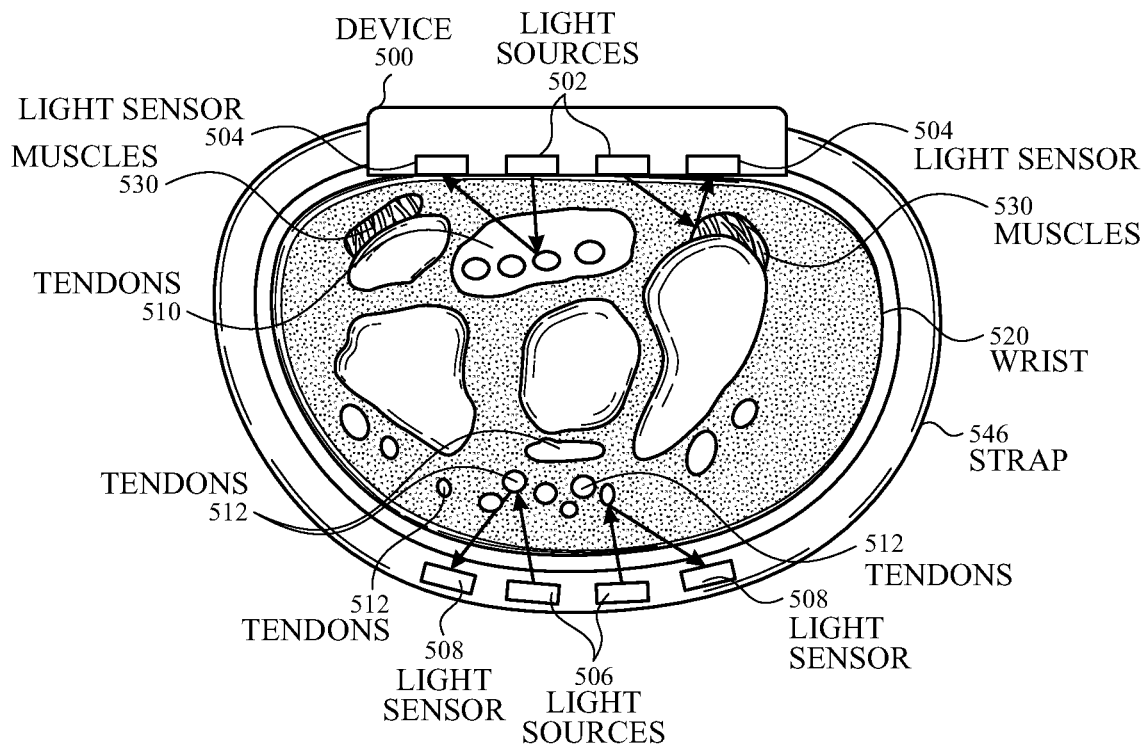
FIG. 5A illustrates a cross-sectional view of a wrist and an exemplary device with motion and gesture sensing using optical sensors according to examples of the disclosure.

FIG. 5A illustrates a cross-sectional view of a wrist and an exemplary device with motion and gesture sensing using optical sensors according to examples of the disclosure. Device 500 can attach to wrist 520 using strap 546. In some examples, device 500, strap 546, or both can touch the skin of wrist 520. Wrist 520 can include tendons 510 and 512 and muscles 530. Device 500 can include one or more light sources 502 and one or more light sensors 504. Light sources 502 can be directed at the skin, tendons 510, and muscles 530. Light emitted from light sources 502 can reflect off the skin, tendons 510, and muscles 530 to create a reflectance profile detected by the light sensors 504. The reflectance profile can change with movements in the tendons of the flexor/extensor and abductors/adductors muscles. From the reflectance profile, the device can determine and distinguish the motions and gestures (e.g., which finger is moved, how the wrist is bent, etc.). For example, opening a hand or making a fist can cause movement of all tendons, whereas moving an individual finger can cause movement of a single tendon. In some examples, strap 546 can include one or more light sources 506 and one or more light sensors 508. Light sources 506 can be directed at and can reflect off the skin, tendons 512, and muscles 530 to create another reflectance profile detected by light sensors 508. Although FIG. 5A illustrates four light sources and four light sensors, examples of the disclosure can include any number of light sources and any number of light sensors.

In some examples, one or more light sources 502 and 506 and one or more light sensors 504 and 508 can have different emission and detection wavelengths. By emitting and detecting light at different wavelengths, a variety of information can be determined. Device 500 can include optical sensing at longer wavelengths (e.g., infrared light), shorter wavelengths (e.g., blue or green light), or both. Longer wavelengths can penetrate deep into the human skin. The longer wavelength light can undergo minimal scattering and absorption and can reflect off of the internal layers of the human body. For example, an infrared source emitting at 950 nm can penetrate 1-2 mm deep into the human skin. Shorter wavelengths may not be able to penetrate as deep as longer wavelengths. For example, deep blue light can reflect off the surface of superficial layers without penetrating into the skin. Green light can penetrate deeper than blue light to reach blood vessels. Green light can be absorbed by hemoglobin and can have low back-reflection from the skin. For example, a blue light source can emit at 450 nm and a green light source can emit at 550 nm, penetrating 0.1-0.2 mm in depth.

Device 500 can be configured for multi-wavelength illumination and sensing to generate both a spatial and temporal reflectance profile sensitive to changes in the user's skin, tendons, muscles, and blood volume as the user moves their wrist and fingers. With the spatial and temporal reflectance, the device can determine the gesture-induced internal structural changes unique to the user.

In some examples, configuring device 500 for multi-wavelength optical sensing can reduce or eliminate motion artifacts. One or more wavelengths (such as short wavelengths) can detect non-internal changes in the skin, and one or more wavelengths (such as long wavelengths) can detect internal changes. Motion artifacts (i.e., non-internal changes) due to, for example, strap 546 vibrating or moving along wrist 520, can lead to changes in the reflectance of light that reflects mostly off the surface of the user's skin. Movement of the user's wrist 520 or fingers (i.e., internal changes) can lead to changes in the reflectance of light that penetrates into the skin. As a result, a signal measured at short wavelengths and not at long wavelengths can be associated with motion artifacts and not user movement. The difference between the long wavelength signal and the short wavelength signal can allow the device to extract out motion artifacts.

Figure 5B:
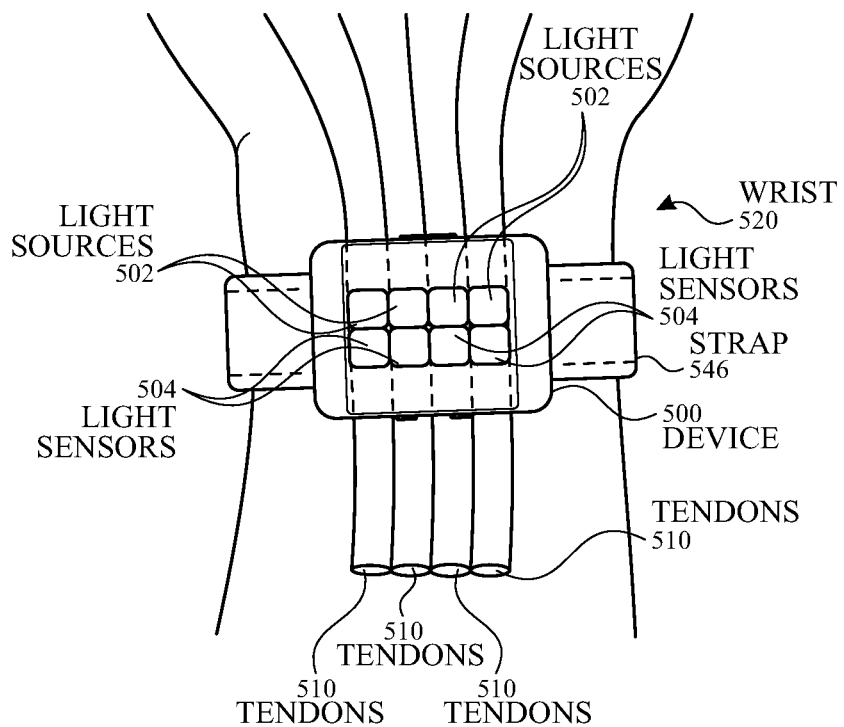
FIG. 5B illustrates a top view of a wrist and an exemplary device with motion and gesture sensing using optical sensors according to examples of the disclosure.

The lights sensors and light sources can be positioned on the device to specifically measure movement of the tendons or the muscles. FIG. 5B illustrates a top view of a wrist and an exemplary device with motion and gesture sensing using optical sensors according to examples of the disclosure. Device 500 can attach to a wrist 520 using strap 546. Device 500 can include a plurality of light sources 502 and a plurality of light sensors 504. The plurality of light sources 502 can be positioned such that light emitted from the light sources 502 is directed towards and can reflect off the tendons 510. The plurality of light sensors 504 can be positioned near the plurality of lights sources 502 and can detect the reflectance profile. Each one of the tendons 510 can be associated with a different light source 502 and light sensor 504 pair. When the user flexes or extends the fingers, tendons 510 can cause a ripple in the surface of the user's skin located at wrist 520. Each of the fingers can cause a ripple at a different location, and the light source and light sensor pair can detect the corresponding tendon 510 moving closer to or away from the skin surface. As a tendon moves, the gap between the tendon and the light source 502 and light sensor pair can change, resulting in a change in the reflectance profile.

In some examples, light sources 502 and lights sensors 504 can be multi-functionality sensors where light sources and light sensors can be configured to measure other signals. For example, light sources 502 and light sensors 504 can also be configured as photoplethysmography (PPG) sensors for measuring a user's heart rate or blood pressure.

Figure 6:
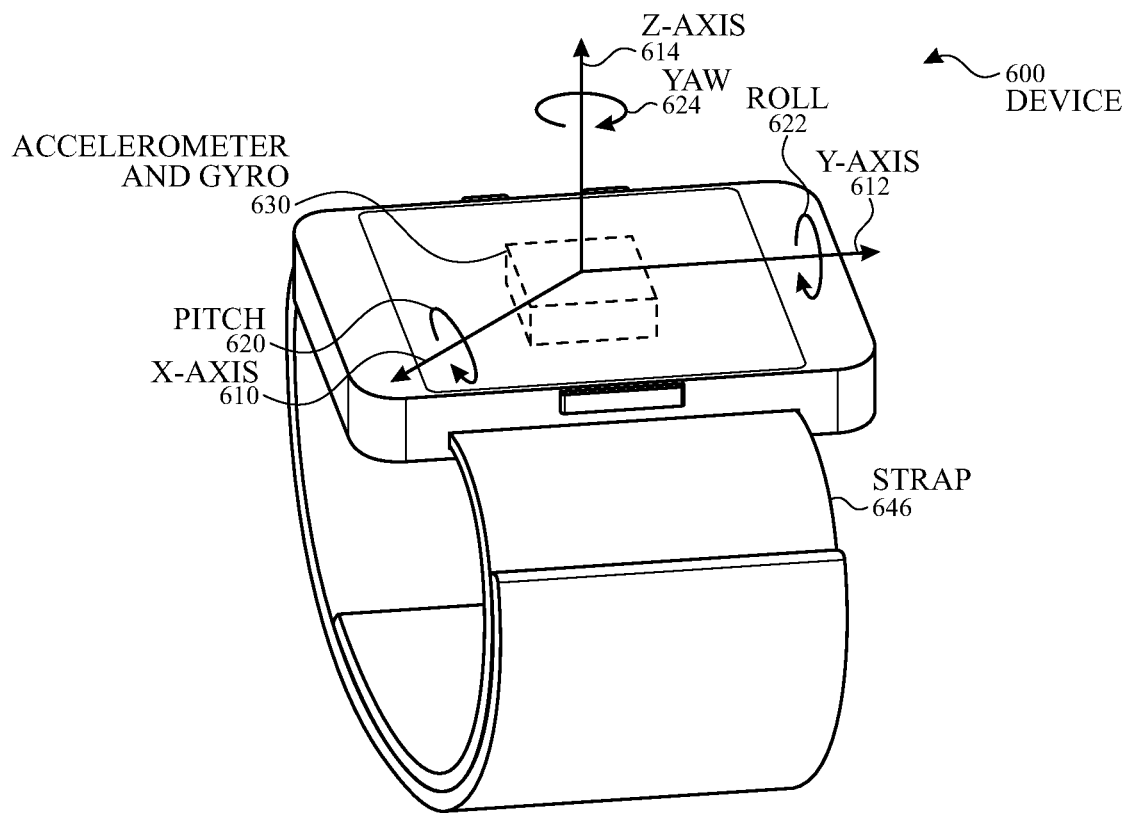
FIG. 6 illustrates a plan view of an exemplary device with motion and gesture sensing using inertial sensors according to examples of the disclosure.

In some examples, inertial sensors, such as an accelerometer and gyroscope, can detect motions and gestures. FIG. 6 illustrates a plan view of an exemplary device with motion and gesture sensing using inertial sensors according to examples of the disclosure. Device 600 can attach to, rest on, or touch a user's wrist (not shown). Device 600 can also include an accelerometer and gyroscope 630 to determine translational and rotational motion. In some examples, the accelerometer and gyroscope can be separate components. The accelerometer can measure non-gravitational acceleration and can determine the change in motion along the x-axis 610, y-axis 612, and z-axis 614. The gyroscope can measure the orientation of the device and can determine the pitch 620, roll 622, and yaw 624.

By using an accelerometer, gyroscope, or both to detect rigid body motions, the device can determine predefined gestures. Examples of such motions can include, but are not limited to, circular wrist motion, hand waving, hand up and down movements, palm up and down movements, and arm waving.

In some examples, one or more light sources such as light sources 502 and 506 of FIG. 5, one or more light sensors 504 and 508 of FIG. 5, and an accelerometer and/or a gyroscope such as accelerometer and gyroscope 630 of FIG. 6 can be incorporated into a device for optical and inertial sensing. Optical sensing can allow the device to determine wrist and finger flexion, extension, abduction, and adduction, while the inertial sensing can allow the device to determine translational and rotational motion.

Figure 7A:
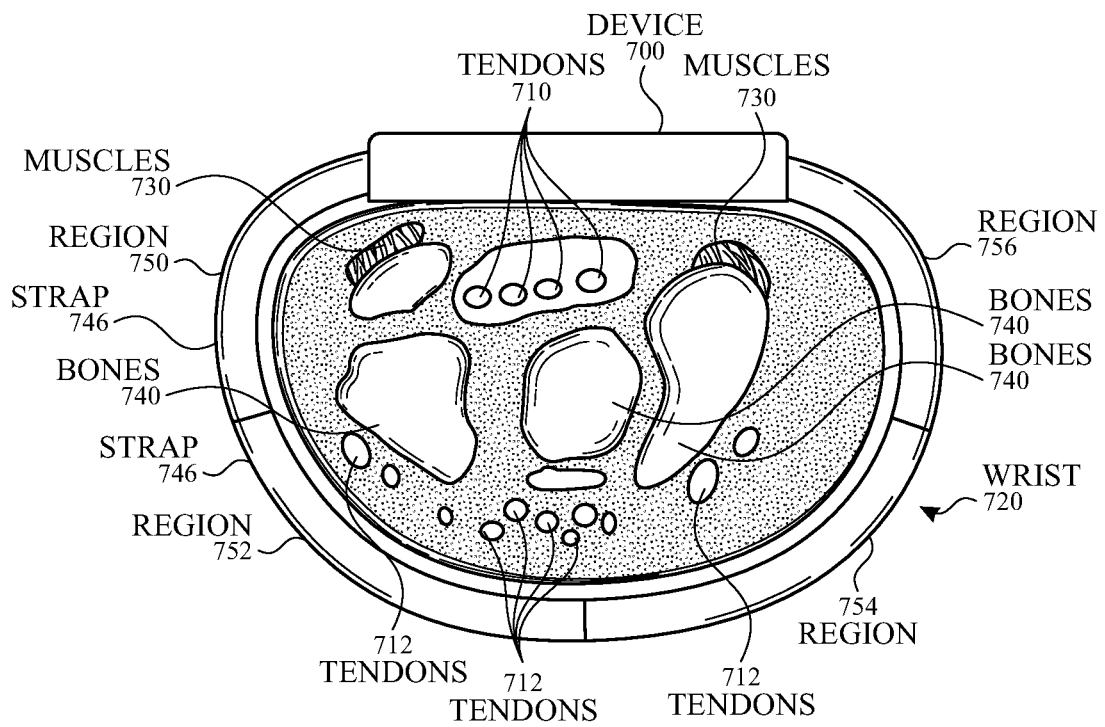
FIG. 7A illustrates a cross-sectional view of a wrist and an exemplary device with motion and gesture sensing using mechanical contact sensors according to examples of the disclosure.

In some examples, the device can utilize mechanical contact sensing to detect motions and gestures. FIG. 7A illustrates a cross-sectional view of a wrist and an exemplary device with motion and gesture sensing using mechanical sensors according to examples of the disclosure. Device 700 can include a strap 746 attached to, resting on, or touching wrist 720. Wrist 720 can include tendons 710 and 712, muscles 730, and bones 740 beneath a user's skin. Strap 746 can include a plurality of regions 750, 752, 754, and 756. Strap 746 can be made of a flexible material, such as Viton. As the user's wrist 720 moves, the strap 746 can stretch or compress at corresponding regions where the stretching/compressing occurs. Device 700 can be configured for detecting the stretch in one or more regions independent of other regions. For example, a user may make a fist gesture. A fist gesture can cause a stretch in strap 746 located at regions 752 and 754, while regions 750 and 756 are unaffected (i.e., no stretching or compressing at regions 750 and 756). In some examples, a plurality of regions can stretch, and the location and intensity of change in length or area at the regions can be indicative of a user's gesture. In some examples, strap 746 can be tightly fitted to wrist 720.

In some examples, strap 746 can be made of a flexible material, and can include gauges capable of measuring a change in length or area of the flexible material. For example, one or more strain gauges can attach to or can be located in strap 746. Circuitry included in the device 700 or in the strap 746 can be configured to measure resistance from the one or more strain gauges. As a region on strap 746 stretches, the resistance can increase, while a region that compresses can cause a decrease in resistance.

Figure 7B:
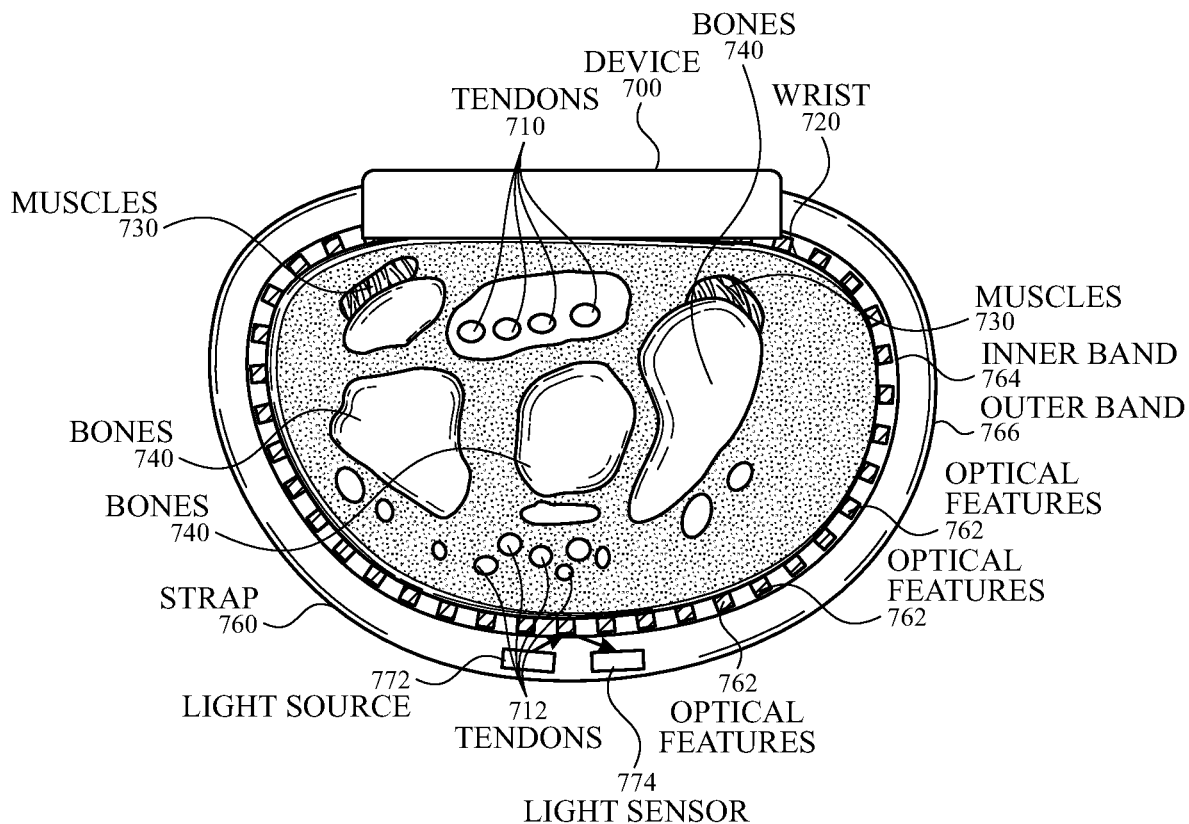
FIG. 7B illustrates a cross-sectional view of a wrist and an exemplary device with motion and gesture sensing using optical sensors located in the strap according to examples of the disclosure.
Figure 7C:
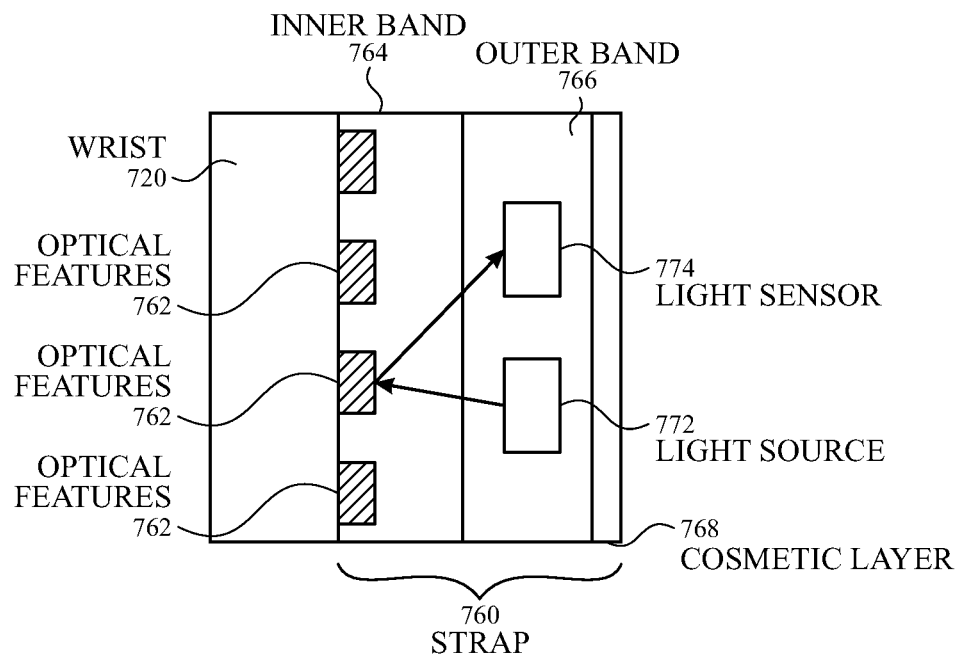
FIG. 7C illustrates a close-up view of the strap according to examples of the disclosure.

In some examples, strap 746 can have an insufficient amount of friction forces against wrist 720. As a result of having an insufficient amount of friction forces, strap 746 may slip against the user's skin, leading to erroneous measurements. FIG. 7B illustrates a cross-sectional view of a wrist and an exemplary device with motion and gesture sensing using optical sensors located in the strap according to examples of the disclosure. FIG. 7C illustrates a close-up view of the strap according to examples of the disclosure. Device 700 can include a strap 760 attached to wrist 720. Strap 760 can include an inner band 764 and an outer band 766. Inner band 764 can be made of a flexible material and can be tightly fitted to wrist 720. Outer band 766 can be made of a rigid material. Inner band 764 can include a plurality of optical features 762, and outer band 766 can include one or more light sources, such as light source 772, and one or more light sensors, such as light sensor 774. In some examples, strap 760 can include a cosmetic layer 768.

Light source 772, located in outer band 776, can emit light towards optical features 762, located in inner band 764. The emitted light can reflect off the optical features 762 and can be detected by light sensor 774, located in outer band 766. The movement of the user's wrist can lead to movement of the optical features 762, which can cause a change in the reflectance of the light detected by light source 772.

Figure 8:
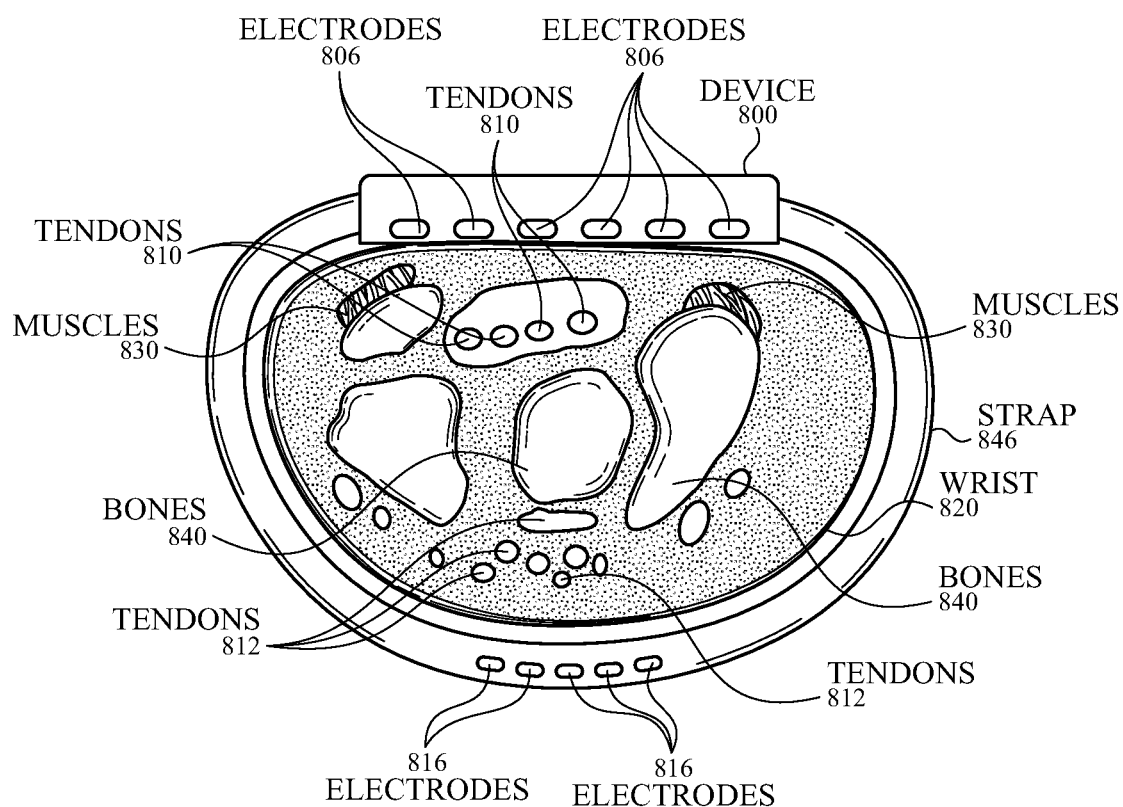
FIG. 8 illustrates a cross-sectional view of a wrist and an exemplary device with motion and gesture sensing using myoelectric sensors according to examples of the disclosure.

In some examples, the device can include myoelectric sensors to detect motions and gestures. FIG. 8 illustrates a cross-sectional view of a wrist and an exemplary device with motion and gesture sensing using myoelectric sensors according to examples of the disclosure. Device 800 can include a strap 846 attached to a wrist 820. Wrist 820 can include tendons 810 and 812, muscles 830, and bones 840. Device 800 can include one or more myoelectric sensors or electrodes 806 and 816. Electrodes 806 and 816 can be configured to measure the electrical signal from tendons 810 and 812. In some examples, electrodes 806 and 816 can be configured to measure a capacitance from a body part, such as tendons 810 and 812, to the electrodes. A change in capacitance can be associated with the user movement. The electrical signal or change in capacitance can allow the device to determine a corresponding motion or gesture based on the intensity and location of the electrical signal or the change in capacitance.

Any one of the optical sensors, inertial sensors, mechanical contact sensors, and myoelectric sensors used individually or together can allow the device to determine a user's motion, gesture, or both. Hand motions can include, but are not limited to, wrist movements, opening and closing of the hand, palm orientated up, down, towards, or away and finger flexing/extending, and movement of the entire hand in an up, down, left or right direction. One or more hand motions can define a gesture input. The device can interpret the gesture input as a command. Exemplary gestures and corresponding commands are illustrated in FIG. 9A.

Figure 9B:
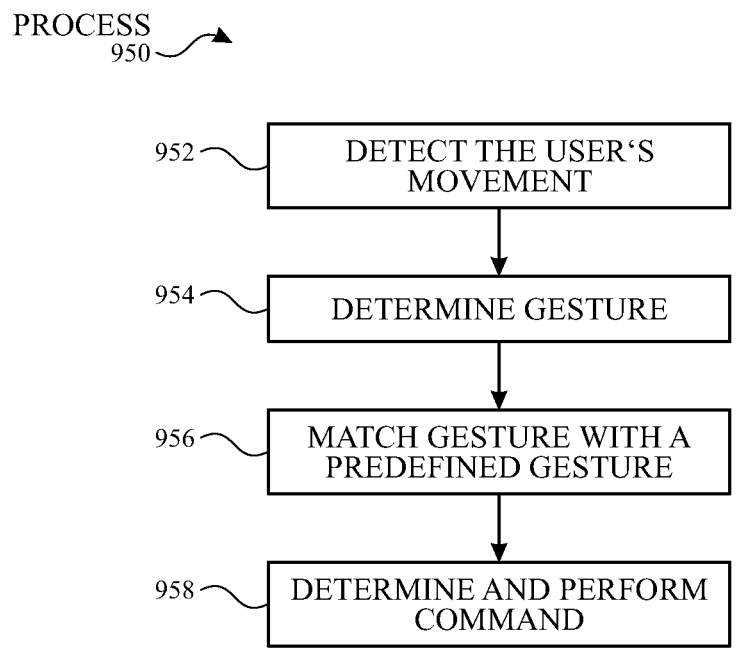
FIG. 9B illustrates an exemplary process flow for determining a command based on the user's movement according to examples of the disclosure.

The gestures and associated commands can be pre-defined and stored in a device database. FIG. 9B illustrates an exemplary process flow for determining a command based on the user's movement according to examples of the disclosure. Process 950 can begin with step 952 where the device detects the user's movement. Based on the user's movement, the device can determine the gesture (step 954). The device can compare the determined gesture to pre-defined gestures located in the database (step 956). If there is a match between the user's gesture and a pre-defined gesture, the device can look up the command that is associated with the predefined gesture and can perform the command (step 958).

Figure 9C:
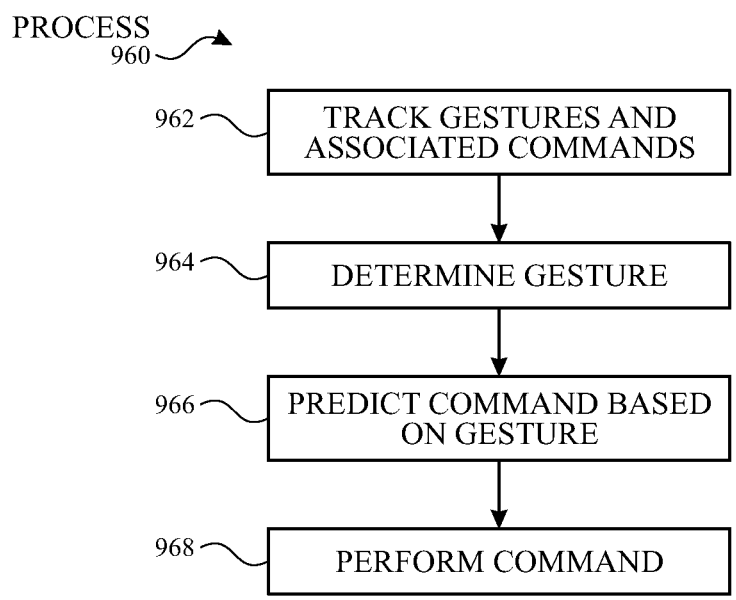
FIG. 9C illustrates an exemplary process flow for recording user-defined gestures according to examples of the disclosure.

In some examples, the device can include an application programming interface (API) that can enable applications to record gestures defined by the user and to associate gestures with specific tasks or commands. FIG. 9C illustrates an exemplary process flow for recording user-defined gestures according to examples of the disclosure. In process 960, the device can track a gesture or motion history and the task or command that typically follows the gesture or motion (step 962). That is, the device can learn from past history which commands are associated with which gestures. Then, in the future, the device can predict what command the user desires to follow a user gesture. When the user moves his or her hand, arm, wrist, or fingers, the device can determine the gesture (step 964). The device can predict the associated command (step 966), and the device can execute the command without direct user interaction (step 968).

Figure 9D:
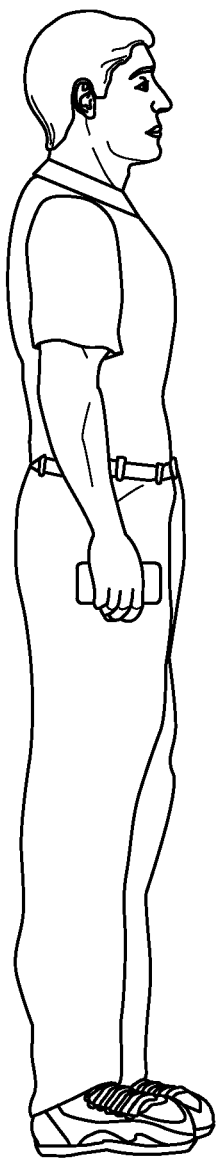
FIGS. 9D-9E illustrate exemplary hand and wrist movement according to examples of the disclosure.
Figure 9E:
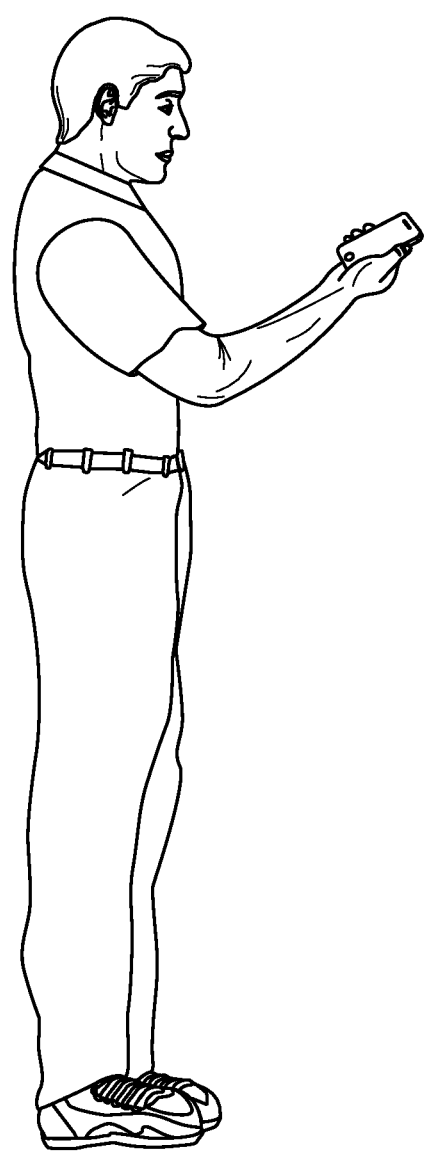

For example, a user can begin with their arm and wrist located at the side of their body as illustrated in FIG. 9D. The user may move their arm and wrist, such that the dorsal side of the wrist is facing up and towards the user's eye, as illustrated in FIG. 9E. The device can determine from past history that such a movement occurs when a user wants to look at the display of the device. The device can associate the movement illustrated in FIGS. 9D-9E with the task or command of automatically turning on the display and waking up the device. That way, the user no longer has to push a button or tap the display screen to wake up the device, and instead, the device can "intelligently" and automatically wake up the device based on this gesture.

In some examples, the device can include a user-specific calibration procedure. The calibration procedure can include an optical calibration, for example, to compensate for anatomic differences between users. The device can display a schematic of fingers, bones, or tendons on the screen. With the device attached to, resting on, or touching, the user's body part, the user can flex or extend each finger. The device can detect each finger or tendon movement and associated information. The associated information can be used to establish a baseline. When the user performs a gesture or movement, the device can compare a signal measured from the gesture or movement and can compare the signal to the baseline.

Figure 9F:
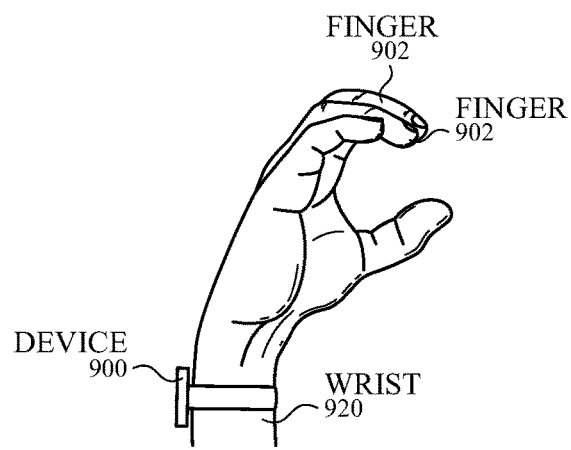
FIGS. 9F-9H illustrate exemplary finger movements associated with sign language according to examples of the disclosure.
Figure 9G:
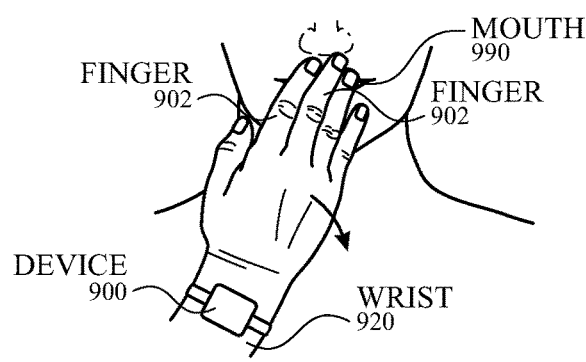
Figure 9H:
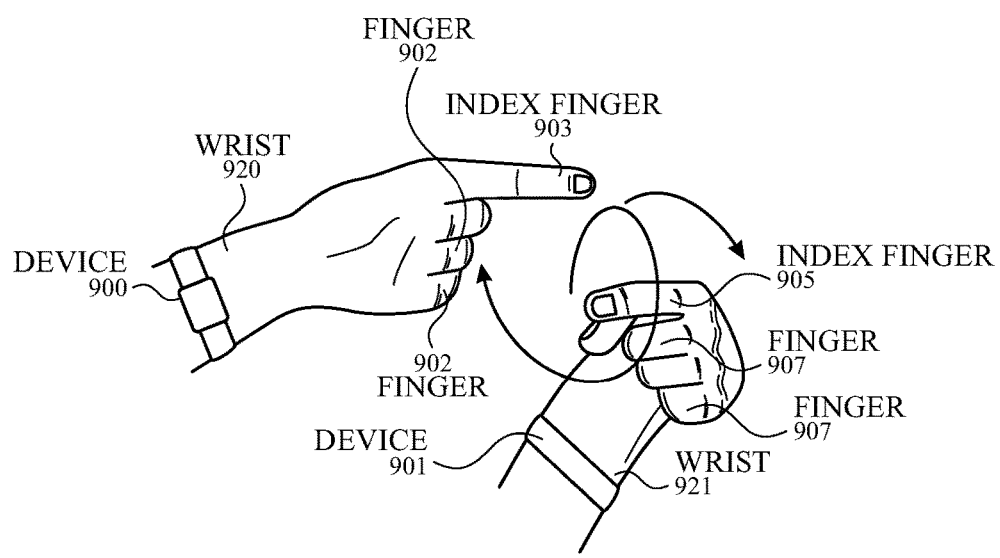

In addition to detected hand and wrist movements, the device can detect finger movements. An example application including detecting finger movements can be detecting sign language. FIGS. 9F-9H illustrate exemplary finger movements associated with sign language according to examples of the disclosure. As shown in FIG. 9F, a user can sign the letter C, for example, using fingers 902, and device 900 can sense the movement of the tendons located at or near wrist 920. Logic located in device 900 can determine that the movement of fingers 902 and the gesture illustrated in FIG. 9F corresponds to the user signing the letter C.

In some examples, detecting sign language can include both finger and wrist movements. For example, a user can sign the phrase "Thank You" by extending the fingers 902 and moving the wrist 920 and device 900 away from a user's mouth 990, as illustrated in FIG. 9G. Device 900 can determine that all fingers 902 are extended by measuring the movement of the tendons located at or near wrist 920. Additionally, device 900 can determine that wrist 920 was moved away from the mouth 990 using the inertial sensors.

In some examples, detecting sign language can include detecting both finger and wrist movements in both hands of the user. For example, a user can sign the word "Go" by extending both index fingers 903 and 905 for both hands, flexing the remaining fingers 902 and 907 for both hands, and moving wrists 920 and 921 in an alternating and circular fashion. Devices 900 and 901 can attach to the wrists 920 and 921 to detect the extension of fingers 903 and 905 and the flexion of fingers 902 and 907 through the movement of the tendons located at or near wrists 920 and 921. Devices 900 and 901 can detect the circular movement of the wrists 920 and 921 using the inertial sensors. In some examples, device 901 can send detected gesture and movement signals or information to device 900 using wired or wireless communications, such as Bluetooth. When device 900 receives the information from device 901, device 900 can determine that the user is moving both wrists 920 and 921, and fingers 902, 903, 905 and 907, and can associate the gestures with a corresponding phrase or command. In some examples, both device 900 and 901 can send detected gesture and movement signals or information to a host device. The host device can process the signals, determine the gesture and movement, and associate the gesture with the corresponding phrase or command. While the figures illustrate device 900 attached to the user's wrist, examples of the disclosure can include the device attached to other body parts.

In some examples, association of the gesture in any of the illustrated above examples can lead to the task of audibly announcing the associated phrase or letter through a speaker or displaying the associated phrase or letter on a display, for example. Device 900 can then be, for example, a sign language interpreter.

Figure 10:
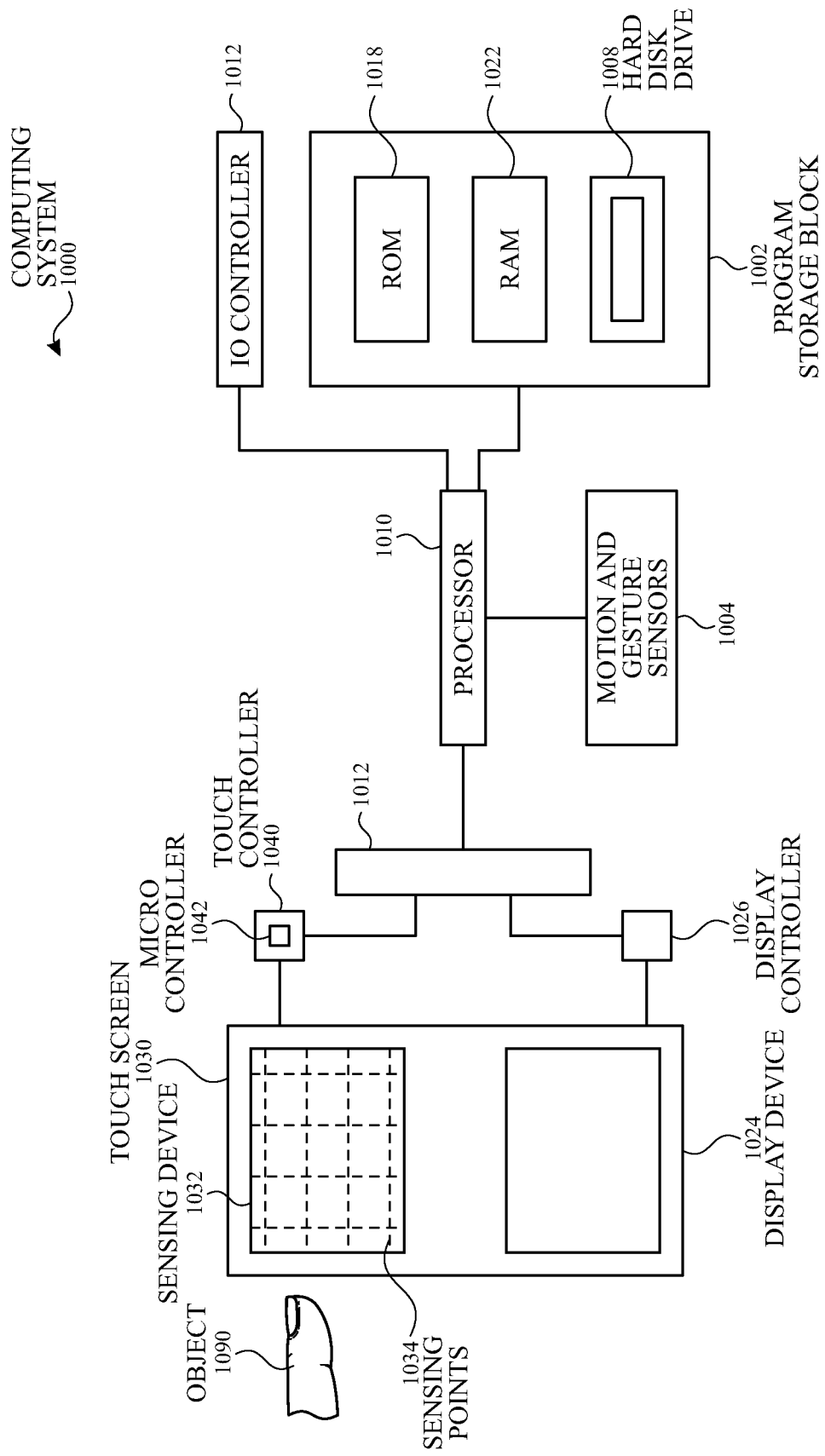
FIG. 10 illustrates an exemplary block diagram of a computing system comprising one or more motion and gesture sensors for determining a user's gesture or motion according to examples of the disclosure.

FIG. 10 illustrates an exemplary block diagram of a computing system comprising one or more motion and gesture sensors for determining a user's gesture or motion according to examples of the disclosure. Computing system 1000 can correspond to any of the computing devices illustrated in FIGS. 1A-1C. Computing system can include a processor 1010 configured to execute instructions to carry out operations associated with computing system 1000. For example, using instructions retrieved from memory, processor 1010 can control the reception and manipulation of input and output data between components of computing system 1000. Processor 1010 can be a single-chip processor or can be implemented with multiple components.

In some examples, processor 1010 together with an operating system can operate to execute computer code and produce end user data. The computer code and data can reside within a program storage block 1002 that can be operatively coupled to processor 1010. Program storage block 1002 can generally provide a place to hold data that is being used by computing system 1000. Program storage block 1002 can be any non-transitory computer-readable storage medium, and can store, for example, history and/or pattern data relating to gesture and motion values measured by one or more motion and gesture sensors 1004. By way of example, program storage block 1002 can include Read-Only Memory (ROM) 1018, Random-Access Memory (RAM) 1022, hard disk drive 1008 and/or the like. The computer code and data could reside on a removable storage medium and be loaded or installed onto the computing system 1000 when needed. Removable storage mediums include, for example, CD-ROM, DVD-ROM, Universal Serial Bus (USB), Secure Digital (SD), Compact Flash (CF), Memory Stick, Multi-Media Card (MMC) and a network component.

Computing system 1000 can also include an input/output (I/O) controller 1012 that can be operatively coupled to processor 1010, or it may be a separate component as shown. I/O controller 1012 can be configured to control interactions with one or more I/O devices. I/O controller 1012 can operate by exchanging data between processor 1010 and the I/O devices that desire to communicate with processor 1010. The I/O devices and I/O controller 1012 can communicate through a data link. The data link can be a one way link or a two way link. In some examples, I/O devices can be connected to I/O controller 1012 through wireless connections. By way of example, a data link can correspond to PS/2, USB, Firewire, IR, RF, Bluetooth or the like.

Computing system 1000 can include a display device 1024 that can be operatively coupled to processor 1010. Display device 1024 can be a separate component (peripheral device) or can be integrated with processor 1010 and program storage block 1002 to form a desktop computer (all-in-one machine), a laptop, a handheld, wearable or tablet computing device or the like. Display device 1024 can be configured to display a graphical user interfaced (GUI) including perhaps a pointer or cursor as well as other information. By way of example, display device 1024 can be any type of display including a liquid crystal display (LCD), an electroluminescent display (ELD), a field emission display (FED), a light emitting diode display (LED), an organic light emitting diode display (OLED) or the like.

Display device 1024 can be coupled to display controller 1026 that can be coupled to processor 1010. Processor 1010 can send raw data to display controller 1026, and display controller 1026 can send signals to display device 1024. Data can include voltage levels for a plurality of pixels in display device 1024 to project an image. In some examples, processor 1010 can be configured to process the raw data.

Computing system 1000 can also include a touch screen 1030 that can be operatively coupled to processor 1010. Touch screen 1030 can be a combination of sensing device 1032 and display device 1024, where the sensing device 1032 can be a transparent panel that is positioned in front of display device 1024 or integrated with display device 1024. In some cases, touch screen 1030 can recognize touches and the position and magnitude of touches on its surface. Touch screen 1030 can report the touches to processor 1010, and processor 1010 can interpret the touches in accordance with its programming. For example, processor 1010 can perform tap and event gesture parsing and can initiate a wake of the device or powering on one or more components in accordance with a particular touch.

Touch screen 1030 can be coupled to a touch controller 1040 that can acquire data from touch screen 1030 and can supply the acquired data to processor 1010. In some examples, touch controller 1040 can be configured to send raw data to processor 1010, and processor 1010 can process the raw data. For example, processor 1010 can receive data from touch controller 1040 and can determine how to interpret the data. The data can include the coordinates of a touch as well as pressure exerted. In some examples, touch controller 1040 can be configured to process raw data itself. That is, touch controller 1040 can read signals from sensing points 1034 located on sensing device 1032 and can turn them into data that the processor 1010 can understand.

Touch controller 1040 can include one or more microcontrollers such as microcontroller 1042, each of which can monitor one or more sensing points 1034. Microcontroller 1042 can, for example, correspond to an application specific integrated circuit (ASIC), which works with firmware to monitor the signals from sensing device 1032, process the monitored signals, and report this information to processor 1010.

One or both display controller 1026 and touch controller 1040 can perform filtering and/or conversion processes. Filtering processes can be implemented to reduce a busy data stream to prevent processor 1010 from being overloaded with redundant or non-essential data. The conversion processes can be implemented to adjust the raw data before sending or reporting them to processor 1010.

In some examples, sensing device 1032 is based on capacitance. When two electrically conductive members come close to one another without actually touching, their electric fields can interact to form a capacitance. The first electrically conductive member can be one or more of the sensing points 1034, and the second electrically conductive member can be an object 1090 such as a finger. As object 1090 approaches the surface of touch screen 1030, a capacitance can form between object 1090 and one or more sensing points 1034 in close proximity to object 1090. By detecting changes in capacitance at each of the sensing points 1034 and noting the position of sensing points 1034, touch controller 1040 can recognize multiple objects, and determine the location, pressure, direction, speed and acceleration of object 1090 as it moves across touch screen 1030. For example, touch controller 1040 can determine whether the sensed touch is a finger, tap or an object covering the surface.

Sensing device 1032 can be based on self-capacitance or mutual capacitance. In self-capacitance, each of the sensing points 1034 can be provided by an individually charged electrode. As object 1090 approaches the surface of touch screen 1030, the object can capacitively couple to those electrodes in close proximity to object 1090, thereby stealing charge away from the electrodes. The amount of charge in each of the electrodes can be measured by the touch controller 1040 to determine the position of one or more objects when they touch or hover over the touch screen 1030. In mutual capacitance, sensing device 1032 can include a two layer grid of spatially separated lines or wires, although other configurations are possible. The upper layer can include lines in rows, while the lower layer can include lines in columns (e.g., orthogonal). Sensing points 1034 can be provided at the intersections of the rows and columns. During operation, the rows can be charged, and the charge can capacitively couple from the rows to the columns. As object 1090 approaches the surface of the touch screen 1030, object 1090 can capacitively couple to the rows in close proximity to object 1090, thereby reducing the charge coupling between the rows and columns. The amount of charge in each of the columns can be measured by touch controller 1040 to determine the position of multiple objects when they touch the touch screen 1030.

Computing system 1000 can also include one or more sensors 1004 proximate to a wrist of a user. Sensors 1004 can be at any one of the above disclosed optical sensors, inertial sensors, mechanical contact sensors, myoelectric sensors, or a combination of two or more. The sensors 1004 can send measured raw data to processor 1010, and processor 1010 can perform noise cancellation to determine a signal corresponding to the user's gesture or motion. For devices that include at least two of optical sensing, inertial sensing, mechanical contact sensing, and myoelectric sensing, processor 1010 can dynamically activate the sensors based on an application and calibration. In some examples, one or more of the sensors can be activated, while other sensors can be deactivated to conserve power. In some examples, processor 1010 can store the raw data and/or processed information in a ROM 1018 or RAM 1022 for historical tracking or for future diagnostic purposes.

Figure 11:
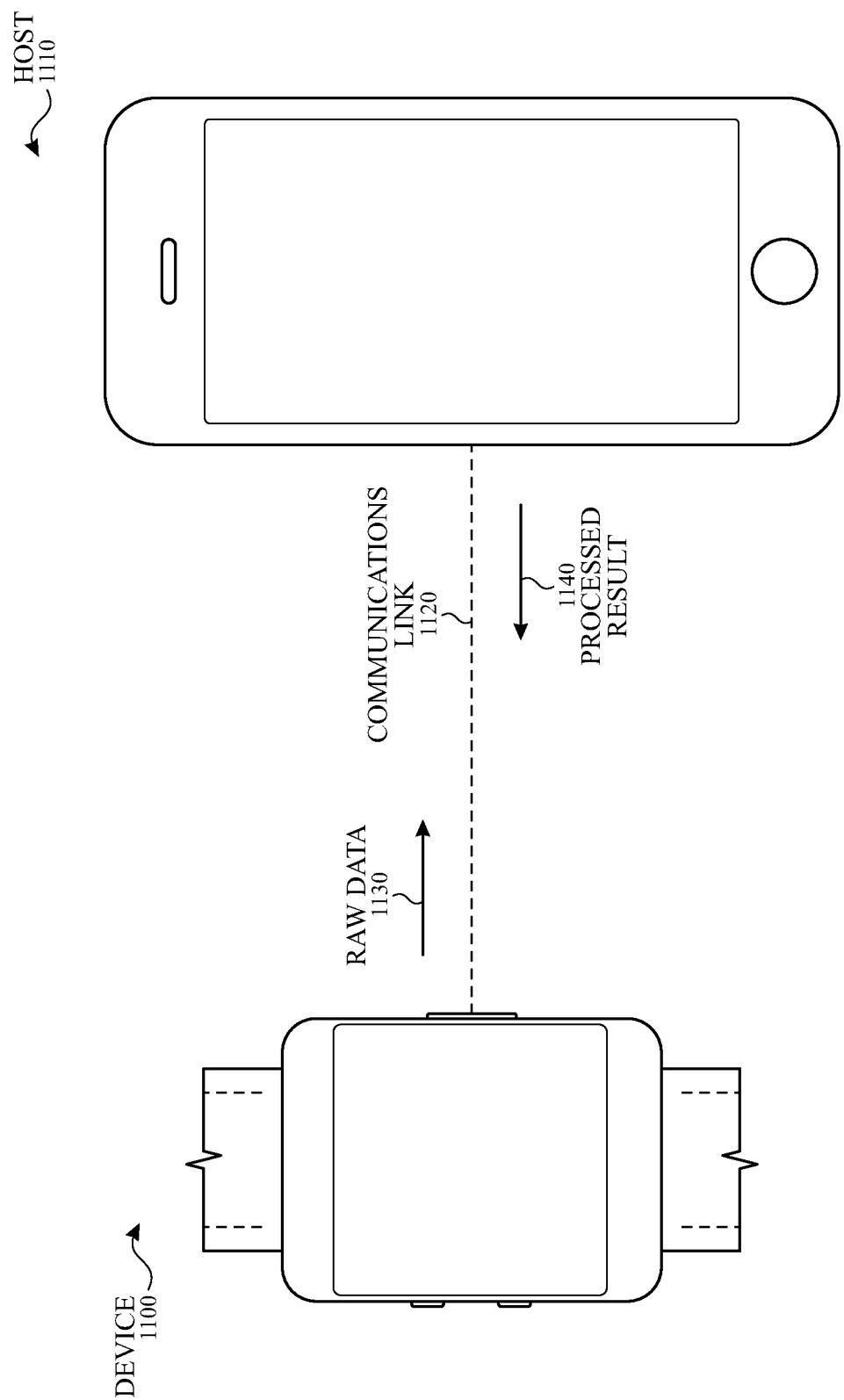
FIG. 11 illustrates an exemplary configuration in which a device is connected to a host according to examples of the disclosure.

In some examples, the sensors can measure the signal and processor 1010 can determine the user's gesture and/or motion. In some examples, determination of user gesture and/or motion need not be performed on the device itself. FIG. 11 illustrates an exemplary configuration in which a device is connected to a host according to examples of the disclosure. Host 1110 can be any device external to device 1100 including, but not limited to, any of the systems illustrated in FIGS. 1A-1C or a server. Device 1100 can be connected to host 1110 through communications link 1120. Communications link 1120 can be any connection including, but not limited to, a wireless connection and a wired connection. Exemplary wired connections include Universal Serial Bus (USB), FireWire, Thunderbolt, or any connection requiring a physical cable.

In operation, instead of determining a user gesture and/or motion on the device 1100 itself, device 1100 can send raw data 1130 measured from the sensors over communications link 1120 to host 1110. Host 1110 can receive raw data 1130, and host 1110 can process the light information. Processing the light information can include canceling or reducing any noise due to artifacts and determining the user gesture and/or motion. Host 1110 can include algorithms or calibration procedures to account for differences in a user's characteristics or performance affecting the sensor signal. Additionally, host 1110 can include storage or memory for tracking a user gesture and motion history for diagnostic purposes. Host 1110 can send the processed result 1140 or related information back to device 1100. Based on the processed result 1140, device 1100 can notify the user or adjust its operation accordingly. By offloading the processing and/or storage of the light information, device 1100 can conserve space and power, enabling device 1100 to remain small and portable, as space that could otherwise be required for processing logic can be freed up on the device.

In some examples, a portable electronic device is disclosed. The portable electronic device may comprise: one or more light emitters capable of emitting light at a user's body part; one or more optical sensors capable of detecting a first reflectance of the emitted light, wherein the first reflectance is associated with movement of one or more tendons located in the body part; and logic capable of determining a gesture from the first reflectance and further capable of associating a command with the determined gesture. Additionally or alternatively to one or more examples disclosed above, in other examples, the device further comprises a strap attached to the device, wherein at least one of the one or more optical sensors and at least one of the one or more light emitters are located on or in the strap. Additionally or alternatively to one or more examples disclosed above, in other examples, the at least one of the one or more optical sensors located on or in the strap is capable of detecting a second reflectance of emitted light from the at least one or more light emitters located on or in the strap, and the logic is further capable of determining the gesture from the first and second reflectance. Additionally or alternatively to one or more examples disclosed above, in other examples, the device comprises at least two light emitters and at least two optical sensors, wherein the at least two light emitters and the at least two optical sensors emit and detect light at different wavelengths. Additionally or alternatively to one or more examples disclosed above, in other examples, the different wavelengths are selected from a group comprising infrared, blue, and green wavelengths. Additionally or alternatively to one or more examples disclosed above, in other examples, the optical sensors are multi-functional sensors capable of detecting a photoplethysmography signal. Additionally or alternatively to one or more examples disclosed above, in other examples, the device further comprises at least one of an inertial sensor, a mechanical contact sensor, and a myoelectric sensor.

In some examples, a portable electronic device is disclosed. The portable electronic device may comprise: a strap attached to the device, wherein the strap comprises a first band; and logic capable of measuring a change in one or more characteristics associated with movement of the first band in response to movement of one or more tendons located in a user's body part, determining a gesture based on the change in the one or more characteristics, and associating a command with the gesture. Additionally or alternatively to one or more examples disclosed above, in other examples, the first band comprises a plurality of regions, the plurality of regions capable of stretching or compressing in response to the movement of the one or more tendons, and wherein the one or more characteristics is a resistance due to a change in stretch or compression in at least one of the plurality of regions. Additionally or alternatively to one or more examples disclosed above, in other examples, the strap further comprises a second band, the first band comprises a plurality of optical features, and the second band comprises one or more light emitters capable of emitting light at the optical features, and one or more light sensors capable of detecting a reflectance of the emitted light, and wherein the one or more characteristics is the detected reflectance. Additionally or alternatively to one or more examples disclosed above, in other examples, the device further comprises at least one of an optical sensor, an inertial sensor, and a myoelectric sensor.

In some examples, a portable electronic device is disclosed. The portable electronic device may comprise: one or more electrodes capable of detecting a change in capacitance associated with movement of one or more tendons located in a user's body part; and logic capable of determining a gesture based on the movement and further capable of associating a command with the determined gesture. Additionally or alternatively to one or more examples disclosed above, in other examples, the one or more electrodes are located in or on a strap attached to the device. Additionally or alternatively to one or more examples disclosed above, in other examples, the device further comprises at least one of an optical sensor, an inertial sensor, and a mechanical contact sensor. Additionally or alternatively to one or more examples disclosed above, in other examples, the device further comprises a transceiver capable of receiving a second gesture or movement information from a second device, the second device capable of detecting the second gesture or movement associated with one or more tendons located on a second body part, wherein the logic is further capable of associating the command with the second gesture or movement.

In some examples, of method of determining a gesture is disclosed. The method may comprise: detecting a signal, wherein the signal is a reflectance, change in capacitance, or change in resistance associated with movement of one or more tendons located in the body part; determining the gesture from the signal; and associating a command with the determined gesture. Additionally or alternatively to one or more examples disclosed above, in other examples, the signal is a reflectance of light, the reflectance of light being a reflectance profile generated from a plurality of optical sensors detecting light at different wavelengths. Additionally or alternatively to one or more examples disclosed above, in other examples, the plurality of optical sensors are capable of detecting a photoplethysmography signal. Additionally or alternatively to one or more examples disclosed above, in other examples, the signal is a change in resistance generated from the movement of the one or more tendons causing a change in stretch or compression in a strap. Additionally or alternatively to one or more examples disclosed above, in other examples, the determining the gesture includes receiving a second gesture or movement information from another device, and the associated command is further based on the second gesture.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:

1. An optical sensing device, comprising:
a housing; and
a display disposed within the housing;
a set of light emitters included in the housing of the optical sensing device, wherein a first light emitter of the set of light emitters is configured to emit a first wavelength of light toward a user's body part and a second light emitter of the set of light emitters is configured to emit a second wavelength of light, different than the first wavelength of light, toward the user's body part;
a set of optical sensors included in the housing of the optical sensing device, configured to detect reflections of the first and second wavelengths of light from the user's body part; and
a processor configured to:
determine a difference between the detected reflections of the first and second wavelengths of light
identify noise due to motion artifacts using the determined difference between the detected reflections of the first and second wavelengths of light; and
reduce the noise due to motion artifacts using the determined difference between the detected reflections of the first and second wavelengths of light.

2. The optical sensing device of claim 1, wherein the second wavelength of light is a longer wavelength of light than the first wavelength of light.

3. The optical sensing device of claim 1, wherein the detected reflections of the first wavelength of light are associated with motion artifacts.

4. The optical sensing device of claim 3, wherein the processor extracts motion artifacts out of the detected reflections using the determined difference between the detected reflections of the first and second wavelengths of light.

5. The optical sensing device of claim 1, wherein the detected reflection of the first wavelength of light is a reflection off of the user's skin.

6. The optical sensing device of claim 1, wherein each light emitter of the set of light emitters and each optical sensor of the set of optical sensors are paired in an emitter-optical sensor pair, and each emitter-optical sensor pair is configured to be associated with a tendon located in the user's body part.

7. The optical sensing device of claim 1, wherein the processor is configured to determine a gesture from the detected reflections of the first and second wavelengths of light.

8. A portable electronic device, comprising:
a housing; and
a display disposed within the housing;
a set of light emitters included in the housing of the portable electronic device, each light emitter configured to emit first light toward a respective tendon in a body part of a user;
a set of optical sensors included in the housing of the portable electronic device, each optical sensor optically coupled to a corresponding light emitter of the set of light emitters to form one of a set of emitter-sensor pairs and configured to detect light reflected off of the respective tendon that receives light from the light emitter,
wherein each emitter-sensor pair is configured to be associated with a corresponding tendon; and
each of the corresponding tendons is a different tendon in the body part than other corresponding tendons that are associated with other emitter-sensor pairs of the set of emitter-sensor pairs.

9. The portable electronic device of claim 8, wherein the set of light emitters emits short wavelengths of light and long wavelengths of light.

10. The portable electronic device of claim 9, wherein:
the emitted long wavelengths of light are reflected off of the body part of the user; and
the reflected long wavelengths of light are used to detect internal changes of the body part of the user.

11. The portable electronic device of claim 9, wherein:
the emitted short wavelengths of light are reflected off of skin of the body part, and
the reflected short wavelengths of light are used to detect motion artifacts.

12. The portable electronic device of claim 8, wherein:
the one of the set of emitter-sensor pairs is a first set of emitter-sensor pairs, and
a second set of emitter-sensors pairs is located in a band that is attachable to the housing.

13. The portable electronic device of claim 8, further comprising logic disposed in the housing and configured to determine a gesture of the user.

14. A portable electronic device comprising:
a housing;
a display disposed within the housing;
an inner flexible strap attached to the housing of the portable electronic device, wherein the inner flexible strap is separate and distinct from the housing of the portable electronic device;
an outer flexible strap attached to the housing of the portable electronic device;
a set of light emitters included in the housing of the portable electronic device, wherein a first light emitter of the set of light emitters is configured to emit one or more wavelengths of light at a user's body part;
a set of optical sensors included in the housing of the portable electronic device, configured to detect the light reflected off of the user's body part;
a set of motion detectors included in the inner flexible strap of the portable electronic device and configured to determine a gesture; and
a set of optical features positioned between the inner flexible strap and the outer flexible strap and configured to reflect light emitted by the set of light emitters.

15. The portable electronic device of claim 14, wherein:
the inner flexible strap comprises an elastic region and an inelastic region; and
the elastic region of the inner flexible strap comprises one or more gauges in a flexible material.

16. The portable electronic device of claim 15, further comprising circuitry configured to measure resistance of the one or more gauges.

17. The portable electronic device of claim 15, wherein the one or more gauges are strain gauges.

18. The portable electronic device of claim 14, wherein the set of motion detectors are configured to determine the gesture using at least one of a stretching or compression of the elastic region of the inner flexible strap.

19. The portable electronic device of claim 14, wherein the set of motion detectors are configured to determine the gesture using at least one of a measured change in length or area of the elastic region of the inner flexible strap.

20. The portable electronic device of claim 14, wherein an outer band of the outer flexible strap is rigid.

21. The portable electronic device of claim 14, wherein the inner flexible strap comprises flexible material.

* * * * *